United States Patent [19]
Knowles et al.

[11] Patent Number: 5,968,764
[45] Date of Patent: Oct. 19, 1999

[54] GLUCOSE TRANSPORTER VESICLE AMINOPEPTIDASE

[75] Inventors: William J. Knowles, Madison; Donna Guralski, Oxford; Wallace Haigh, Madison; John T. Letsinger, West Haven, all of Conn.

[73] Assignee: Bayer Corporation, Pittsburgh, Pa.

[21] Appl. No.: 08/437,116

[22] Filed: May 4, 1995

Related U.S. Application Data

[62] Division of application No. 08/309,232, Sep. 20, 1994, abandoned.

[51] Int. Cl.$^6$ ...................................................... C12Q 1/37
[52] U.S. Cl. ................................................................. 435/24
[58] Field of Search .................................................. 435/24

[56] References Cited

U.S. PATENT DOCUMENTS 5,225,354   7/1993   Knowles et al. ......................... 436/548

FOREIGN PATENT DOCUMENTS

92/17575   10/1992   WIPO .

OTHER PUBLICATIONS

Tsujimoto et al. (1992) *Arch. Biochem. Biophys.*, 292(2), "Identification of Human Placental Leucine Aminopeptidase as Oxytocinase", pp. 388–392.
Mastick et al. (1994) *J. Biol. Chem.*, 269(8), "Characterization of a Major Protein in GLUT4 Vesicles", pp. 6089–6092.
Kandror et al. (1994A) *J.Biol.Chem.*, 269(1), "Identification and Isolation of Glycoproteins That Translocate to the cell Surface from GLUT4–Enriched Vesicles in an Insulin–Dependent Fashion", pp. 138–142.
Kandror et al. (1994b) *Proc. Nat. Acad. Sci., USA*, 91, "GP160, A Tissue–Specific Marker for Insulin–Activated Glucose Transport", pp. 8017–8021.
Kandror et al. (1994c) *J. Biol. Chem.*, 269(49), "The Major Protein of GLUT4–Containing Vesicles, GP160, Has Aminopeptidase Activity", paes 30777–30780.
Keller et al. (1995) *J. Biol.Chem.*, 270(40), "Cloning and Characterization of a Novel Insulin–Regulated Membrane Aminopeptidase from GLUT4 Vesicles", pp. 23612–23618.
Rogi et al. (1996) *J. Biol. Chem.*, 271(1), "Human Placental Leucine Aminopeptidase/Oxytocinase", pp. 56–61.
Nanus et al. (1993) *Proc. Nat. Acad.Sci., USA*, 90, "Molecular Cloning of the Human Kidney Differentiation Antigen GP160: Human Aminopeptidase A", pp. 7069–7073.
Kandror et al. (1995) *Biochem. J.*, 307(1), "Comparison of Glucose–Transporter–Containing Vesicles from Rat Fat and Muscle Tissues: Evidence for a Unique Endosomal Compartment", pp. 383–390.
James et al. (1989) *Nature*, 338, "Molecular Cloning and Characterization of an Insulin–Regulatable Glucose Transorter", pp. 83–87.
Verhey et al. (1994) *J. Biol.Chem.*, 269(4), "A Leu–Leu Sequence is Essential for COOH–Terminal Targeting Signal of GLUT4 Glucose Transporter in Fibroblasts", pp. 2353–2356.
Rodnick et al. (1992) *J. Biol.Chem.*, 267(9), "Immunocytochemical and Biochemical Studies of GLUT4 in Rat Skeletal Muscle", pp. 6278–6285.
James, D., et al, *Letters to Nature*, 338, 83–87, (1989).
Verhey, K. et al, *J. Biol., Chem.*, 269, 2353–2356 (1994).
Tsujimoto, M. et al, *Archives of Biochem and BioPhys.* 292, 388–392, (1992).
Mastick, et al., "Characterization of a Major Protein in GLUT4 Vesicles", J. Biol. Chem., 269, 6089–6092 (1994).
Kandror and Pilch, "Identification and Isolation of Glycoproteins That Translocate to the Cell Surface from GLUT4–enriched Vesicles in an Insulin–dependent Fashion", J. Biol. Chem., 269, 138–142 (1994).

*Primary Examiner*—Jon P. Weber

[57] ABSTRACT

An aminopeptidase which is a component of GLUT4-containing vesicles in the natural state, and which cleaves insulin. The claimed protein has a molecular weight of approximately 110 kD in its deglycosylated form. It includes the amino acid sequences Phe-Ala-Ala-Thr-Gln-Phe-Glu-Pro-Leu-Ala-Ala [SEQ ID NO: 1] and Ile-Leu-Gln-Asn-Gln-Ile-Gln-Gln-Gln-Thr-Arg-Thr-Asp-Glu-Gly-Xaa-Pro-Xaa-Met [SEQ ID NO: 2], and reacts with antibodies produced against the peptide identified as [SEQ ID NO: 1]. Modulators of the activity of the aminopeptidase and a method for treating syndromes of insulin resistance, including diabetes, by administration of such a modulator are also claimed.

4 Claims, 14 Drawing Sheets

TIME = 0

TIME = 3.5hrs

TIME = 22hrs

```
                          SEQUENCE LISTING (1) GENERAL INFORMATION:

(iii) NUMBER OF SEQUENCES: 14

(2) INFORMATION FOR SEQ ID NO: 1:

(i) SEQUENCE CHARACTERISTICS:
          (A) LENGTH: 11 amino acids
          (B) TYPE: amino acid
          (D) TOPOLOGY: linear (ii) MOLECULE TYPE: protein fragment
          (A) DESCRIPTION: tryptic digest polypeptide from full length
               protein (v) FRAGMENT TYPE: internal fragment (vi) ORIGINAL SOURCE: affinity purified protein from-
          (A) ORGANISM: Rattus norvegicus
          (B) STRAIN: Sprague-Dawley
          (F) TISSUE TYPE: adipose (ix) FEATURE:
          (A) NAME/KEY: GTVap fragment p94
          (C) IDENTIFICATION METHOD: protein sequencing (xi) SEQUENCE DESCRIPTION: SEQ ID NO: 1:

Phe Ala Ala Thr Gln Phe Glu Pro Leu Ala Ala
                5                   10

(2) INFORMATION FOR SEQ ID NO: 2:

(i) SEQUENCE CHARACTERISTICS:
          (A) LENGTH: 19 amino acids
          (B) TYPE: amino acid
          (D) TOPOLOGY:  linear (ii) MOLECULE TYPE: protein fragment
          (A) DESCRIPTION: tryptic digest polypeptide from full length
               protein (v) FRAGMENT TYPE: internal fragment (vi) ORIGINAL SOURCE: affinity purified protein from-
          (A) ORGANISM: Rattus norvegicus
          (B) STRAIN: Sprague-Dawley
          (F) TISSUE TYPE: adipose (ix) FEATURE:
          (A) NAME/KEY: GTVap fragment p85
          (C) IDENTIFICATION METHOD: protein sequencing
          (D) OTHER INFORMATION: GeneSeq patent database partial match
               (accession # GSP:R28142; EP 0 535 241 A1) identified as
               leucine aminopeptidase from placental origin (xi) SEQUENCE DESCRIPTION: SEQ ID NO: 2:

Ile Leu Gln Asn Gln Ile Gln Gln Gln Thr Arg Thr Asp Glu Gly Xaa
                5                   10                  15
```

Pro Xaa Met (2) INFORMATION FOR SEQ ID NO: 3:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: Other nucleic Acid
        (A) DESCRIPTION: synthetic oligonucleotide probe based on
            peptide sequence (iii) HYPOTHETICAL: yes (iv) ANTI-SENSE: no (xi) SEQUENCE DESCRIPTION: SEQ ID NO: 3:

TTYGCNGCNA CNCARTTYGA RCCNYTNGCN GCN                              33

(2) INFORMATION FOR SEQ ID NO: 4:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: Other nucleic Acid
        (A) DESCRIPTION: synthetic oligonucleotide probe based on
            peptide sequence (iii) HYPOTHETICAL: yes (iv) ANTI-SENSE: yes (xi) SEQUENCE DESCRIPTION: SEQ ID NO: 4:

NGCNGCNARN GGYTCRAAYT GNGTNGCNGC RAA                               33

(2) INFORMATION FOR SEQ ID NO: 5:

(i) SEQUENCE CHARACTERISTICS:
        (A) LENGTH: 15 amino acids
        (B) TYPE: amino acid
        (D) TOPOLOGY: linear (ii) MOLECULE TYPE: protein fragment
        (A) DESCRIPTION: tryptic digest polypeptide from full length
            protein (v) FRAGMENT TYPE: internal fragment (vi) ORIGINAL SOURCE:
        (A) ORGANISM: Rattus norvegicus
        (B) STRAIN: Sprague-Dawley
        (F) TISSUE TYPE: adipose (ix) FEATURE:
        (A) NAME/KEY: GTVap fragment p85
        (C) IDENTIFICATION METHOD: protein sequencing
        (D) OTHER INFORMATION: positively identified amino acids in
            GTVap protein sequence; used for the design of
            oligonucleotide probes (xi) SEQUENCE DESCRIPTION: SEQ ID NO: 5:

Ile Leu Gln Asn Gln Ile Gln Gln Gln Thr Arg Thr Asp Glu Gly
             5                  10               15

(2) INFORMATION FOR SEQ ID NO: 6:

(i) SEQUENCE CHARACTERISTICS:

(A) LENGTH: 45 base pairs
                (B) TYPE: nucleic acid
                (C) STRANDEDNESS: single
                (D) TOPOLOGY: linear (ii) MOLECULE TYPE: Other nucleic Acid
                (A) DESCRIPTION: synthetic oligonucleotide probe based on
                    peptide sequence (iii) HYPOTHETICAL: yes (iv) ANTI-SENSE: no (xi) SEQUENCE DESCRIPTION: SEQ ID NO: 6:

ATHYTNCARA AYCARATHCA RCARCARACN MGNACNGAYG ARGGN                        45

(2) INFORMATION FOR SEQ ID NO: 7:

(i) SEQUENCE CHARACTERISTICS:
                (A) LENGTH: 45 base pairs
                (B) TYPE: nucleic acid
                (C) STRANDEDNESS: single
                (D) TOPOLOGY: linear (ii) MOLECULE TYPE: Other nucleic Acid
                (A) DESCRIPTION: synthetic oligonucleotide probe based on
                    peptide sequence (iii) HYPOTHETICAL: yes (iv) ANTI-SENSE: yes (xi) SEQUENCE DESCRIPTION: SEQ ID NO: 7:

NCCYTCRTCN GTNCKNGTYT GYTGYTGDAT YTGRTTYTGN ARDAT                        45

(2) INFORMATION FOR SEQ ID NO: 8:

(i) SEQUENCE CHARACTERISTICS:
                (A) LENGTH: 12 amino acids
                (B) TYPE: amino acid
                (D) TOPOLOGY: linear (ii) MOLECULE TYPE: synthetic peptide
                (A) DESCRIPTION: synthetic peptide designed from GTVap p94
                    fragment and modified with a carboxyl terminal cysteine (xi) SEQUENCE DESCRIPTION: SEQ ID NO: 8:

Phe Ala Ala Thr Gln Phe Glu Pro Leu Ala Ala Cys
                5                   10

(2) INFORMATION FOR SEQ ID NO: 9:

(i) SEQUENCE CHARACTERISTICS:
                (A) LENGTH: 16 amino acids
                (B) TYPE: amino acid
                (D) TOPOLOGY: linear (ii) MOLECULE TYPE: synthetic peptide
                (A) DESCRIPTION: synthetic peptide designed from GLUT4
                    protein sequence amino acids 495-509 and modified with
                    an amino terminal cysteine (xi) SEQUENCE DESCRIPTION: SEQ ID NO: 9:

Cys Lys Pro Ser Thr Glu Leu Glu Tyr Leu Gly Pro Asp Glu Asn Asp
                5                   10                  15

(2) INFORMATION FOR SEQ ID NO: 10:

(i) SEQUENCE CHARACTERISTICS:
                (A) LENGTH: 8 amino acids
                (B) TYPE: amino acid
                (D) TOPOLOGY: linear

```
    (ii) MOLECULE TYPE: synthetic peptide
         (A) DESCRIPTION: synthetic peptide designed from GLUT4
             protein sequence amino acids 495-501 and modified with
             a carboxyl terminal cysteine (xi) SEQUENCE DESCRIPTION: SEQ ID NO: 10:

Lys Pro Ser Thr Glu Leu Glu Cys
                5

(2) INFORMATION FOR SEQ ID NO: 11:

(i) SEQUENCE CHARACTERISTICS:
         (A) LENGTH: 7 amino acids
         (B) TYPE: amino acid
         (D) TOPOLOGY: linear (ii) MOLECULE TYPE: synthetic peptide
         (A) DESCRIPTION: synthetic peptide designed from GLUT4
             protein sequence amino acids 498-503 and modified with
             a carboxyl terminal cysteine (xi) SEQUENCE DESCRIPTION: SEQ ID NO: 11:

Thr Glu Leu Glu Tyr Leu Cys
                5

(2) INFORMATION FOR SEQ ID NO: 12:

(i) SEQUENCE CHARACTERISTICS:
         (A) LENGTH: 7 amino acids
         (B) TYPE: amino acid
         (D) TOPOLOGY: linear (ii) MOLECULE TYPE: synthetic peptide
         (A) DESCRIPTION: synthetic peptide designed from GLUT4
             protein sequence amino acids 504-509 and modified with
             an amino terminal cysteine (xi) SEQUENCE DESCRIPTION: SEQ ID NO: 12:

Cys Gly Pro Asp Glu Asn Asp
                5

(2) INFORMATION FOR SEQ ID NO: 13:

(i) SEQUENCE CHARACTERISTICS:
         (A) LENGTH: 12 amino acids
         (B) TYPE: amino acid
         (D) TOPOLOGY: linear (ii) MOLECULE TYPE: protein fragment
         (A) DESCRIPTION: tryptic digest polypeptide from full length
             protein (v) FRAGMENT TYPE: internal fragment (vi) ORIGINAL SOURCE:
         (A) ORGANISM: Rattus norvegicus
         (B) STRAIN: Sprague-Dawley
         (F) TISSUE TYPE: adipose (ix) FEATURE:
         (C) IDENTIFICATION METHOD: protein sequencing
         (D) OTHER INFORMATION: GTVap1 peptide sequence including
             residues assigned with less than full confidence (xi) SEQUENCE DESCRIPTION: SEQ ID NO: 13:

Phe Ala Ala Thr Gln Phe Glu Pro Leu Ala Ala Arg
                5                   10

(2) INFORMATION FOR SEQ ID NO: 14:

(i) SEQUENCE CHARACTERISTICS:
```

```
            (A) LENGTH: 19 amino acids
            (B) TYPE: amino acid
            (D) TOPOLOGY: linear (ii) MOLECULE TYPE: protein fragment
            (A) DESCRIPTION: tryptic digest polypeptide from full length
                protein (v) FRAGMENT TYPE: internal fragment (vi) ORIGINAL SOURCE:
            (A) ORGANISM: Rattus norvegicus
            (B) STRAIN: Sprague-Dawley
            (F) TISSUE TYPE: adipose (ix) FEATURE:
            (C) IDENTIFICATION METHOD: protein sequencing
            (D) OTHER INFORMATION: GTVap2 sequence including residues
                assigned with less than full confidence; see OTHER
                INFORMATION on SEQ ID NO: 2

(xi) SEQUENCE DESCRIPTION: SEQ ID NO: 14:

Ile Leu Gln Asn Gln Ile Gln Gln Gln Thr Arg Thr Asp Glu Gly Thr
                 5                  10                  15

Pro Asn Met
```

GLUCOSE TRANSPORTER VESICLE AMINOPEPTIDASE

This application is a Division of U.S. application Ser. No. 08/309,232 filing date Sep. 20, 1994, now abandoned.

BACKGROUND

Adipocytes and myocytes contain intracellular GLUT4-containing vesicles which fuse to the plasma membrane upon insulin stimulation. The resulting increase in plasma membrane GLUT4 is responsible for the 10 to 20-fold increase in glucose transport in the insulin-stimulated state. GLUT4-containing vesicle movement from the cytoplasm to fusion with the plasma membrane, a process termed translocation, is believed to be abnormal in both insulin resistance and non-insulin dependent diabetes mellitus (NIDDM). See B. Kahn, J. Clin. Invest., 89, 1367–1374, 1992.

The normal molecular mechanisms of insulin-stimulated translocation of GLUT4-containing vesicles to the plasma membrane and the concomitant increase in glucose uptake by the affected cells are still largely unknown. Proposed mechanisms include both GLUT4-containing vesicle docking and fusion with the plasma membrane.

The GLUT4-containing vesicles are only a minor fraction of the total intracellular vesicle population within adipocytes [James et al, J. Biol. Chem., 262, 11817–11824, (1987)]. These GLUT4 vesicles can be isolated from the low density microsomal fraction using immunoaffinity methods with antibodies to the cytoplasmic-oriented C-terminus of GLUT4 [James, et al, J. Biol. Chem., 262, 11817–11824, (1987); Thoidis, et al, J. Biol. Chem., 268, 11691–11696, (1993)]. GLUT4-enriched vesicles have been shown to have several synaptic vesicle-like proteins including vesicle associated membrane protein (VAMP) [Cain et al, J. Biol. Chem., 267, 11681–11684, (1992)] and secretory carrier associated membrane protein (SCAMP) [Laurie et al, J. Biol. Chem., 268, 19110–19117, (1993)], and certain ras analog proteins originally identified in brain (Rab proteins) [Cormont, et al, J. Biol. Chem., 268, 19491–19497, (1993)].

Presently the pharmacologic therapy for NIDDM may not target the insulin resistance which is the key pathophysiological abnormality of the disease. The existing therapies are 1) diet and exercise; 2) sulfonylureas, which stimulate insulin secretion; 3) α-glucosidase inhibitors, which inhibit the enzymatic digestion of complex carbohydrates and thereby slow the postprandial absorption of glucose; 4) metformin, whose mechanism likely includes improvement of hepatic insulin sensitivity, and 5) insulin injections.

A therapeutic agent which targets insulin resistance and improves insulin sensitivity would have significant advantages over the therapies listed above. Such a therapeutic agent is the subject of the present invention. It is an objective of this invention to increase insulin sensitivity by modulating the aminopeptidase associated with GLUT4 vesicles.

SUMMARY

The present invention relates to a novel aminopeptidase, herein designated GTVap, which is a component of GLUT4-containing vesicles and is involved in the insulin-signalling pathway. It also relates to the use of therapeutic modulators of this protein to treat diabetes. Additional aspects of the invention will be discussed below.

Down-regulation of peptide signalling molecules is important to maintain normal homeostasis. More particularly, down-regulation or removal of active insulin is important for prevention of hyperinsulinemia with resulting hypoglycemia in nondiabetic individuals. Current dogma is that all circulating insulin is degraded after binding to the insulin receptor, internalization, and eventual intracellular proteolysis by a previously characterized insulin degrading enzyme (IDE).

Data presented herein indicate that an additional mechanism for insulin degradation exists, namely, that adipocyte cell surface GTVap removes the N-terminal amino acids from the insulin molecule, altering its physiological activity. Although this may be a normal mechanism of insulin processing, the increased levels of enzyme present in obese individuals or in conditions of increased enzyme activity leads to conditions in which plasma insulin has been partially inactivated. This explains the association of obesity with insulin resistance and NIDDM.

Another indication that GTVap may be important in the insulin signalling pathway is the fact that GTVap is found only in insulin-sensitive tissues which also contain the GLUT4 protein.

It is known that obesity is associated with a variety of clinical manifestations, as well as with increased body fat and GTVap. The increased body fat and GTVap may result in inappropriate inactivation or activation of other important circulating polypeptides besides insulin. Accordingly, pharmacological and genetic manipulation of GTVap constitutes a new therapeutic target for amelioration of insulin resistance, NIDDM, and obesity.

The present invention relates to a protein which is a component of GLUT4-containing vesicles in the natural state. This protein has aminopeptidase activity; a molecular weight of approximately 165 kD, 155 kD, or 120 kD depending upon its degree of glycosylation, and approximately 110 kD in its deglycosylated form. It includes the amino acid sequences Phe-Ala-Ala-Thr-Gln-Phe-Glu-Pro-Leu-Ala-Ala [SEQ ID NO: 1] and Ile-Leu-Gln-Asn-Gln-Ile-Gln-Gln-Gln-Thr-Arg-Thr-Asp-Glu-Gly-Xaa-Pro-Xaa-Met [SEQ ID NO: 2], and reacts with antibodies produced against the peptide identified as [SEQ ID NO: 8]. The present invention also relates to muteins of this protein.

The invention further relates to a method of treating syndromes of insulin resistance, comprising administering to a subject exhibiting a syndrome of insulin resistance an effective amount of a modulator of GTVap in a pharmaceutically acceptable carrier.

Other aspects of the invention will be discussed in the detailed description below.

DESCRIPTION OF THE DRAWING

The invention will be more completely understood from a consideration of the following detailed description and glossary of terms, taken in conjunction with the drawing, in which.

DETAILED DESCRIPTION

Figure 1:
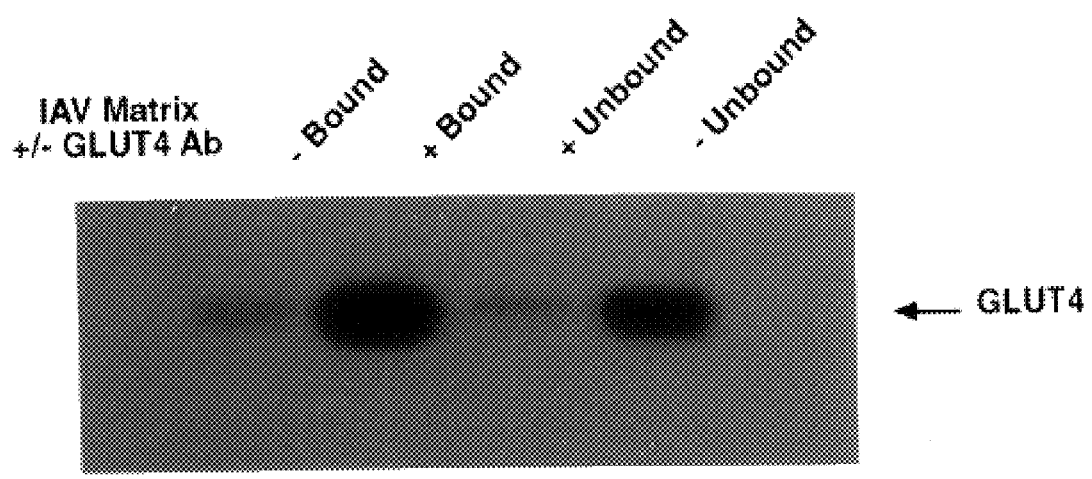
FIG. 1 is a Western blot showing the immunoaffinity purification of GLUT4 vesicles.

GLUT4-containing vesicles from rat adipocytes have been purified by an immunoaffinity procedure and their protein composition has been compared to LDM vesicles lacking GLUT4. The hypothesis has been that the GLUT4 vesicle proteins are involved in the insulin-induced translocation of the vesicles, which includes movement from their resident intracellular compartment, docking with and fusion with the plasma membrane, and re-uptake or endocytosis from the plasma membrane upon termination of the insulin signal. The present purification strategy resulted in the identification of several unique proteins with molecular weights in the vicinity of 160 kD.

Two of the proteins identified as being unique with GLUT4-containing vesicles had molecular weights of approximately 165 kD and 155 kD, respectively. Initial attempts at N-terminal sequencing indicated that the N-terminus of each was blocked. Digestion of both the 165 kD and 155 kD proteins followed by microbore HPLC separation of the peptide fragments indicated that these proteins are closely related, as the HPLC-UV profiles of the digests are quite similar. One peptide sequence had 100% homology to a previously published protein claimed to be a pregnancy-related plasma aminopeptidase. None of the remaining peptide sequences have any homology to the placental or any other known aminopeptidase.

Experiments with a variety of synthetic and natural aminopeptidase substrates have shown that the 165 kD, 155 kD, and 120 kD proteins within the adipocyte are aminopeptidases and are glycosylated since they bind to wheat germ lectin affinity resins. The 165 kD and 155 kD materials can be deglycosylated using N-glycosidase F and result in a protein of 110 kD. The 120 kD material is related to the 165 kD and 155 kD aminopeptidases since antibodies reactive with the 165 kD and 155 kD forms also react with the 120 kD aminopeptidase. In the text below, each aminopeptidase from the GLUT4-containing vesicles will be referred to as a Glucose Transporter Vesicle aminopeptidase (GTVap), with the molecular weight in kD being appended to the designation.

Although one peptide sequence of GTVap 165 kD had 100% homology to a known pregnancy-related aminopeptidase of placental origin, the two aminopeptidases have significantly different properties and are presumably members of a large family of aminopeptidases. The GTVap enzyme activity and immunoreactivity have also been found in rat muscle, human fat, and the adipocyte cell line 3T3-L1.

Regarding the isolated and purified aminopeptidase which is a component of GLUT4-containing vesicles in the natural state, the aminopeptidase activity, molecular weight, certain amino acid sequences, and its reactivity with antibodies produced against the peptide identified as [SEQ ID NO: 1] have been summarized above. This protein is useful for identification of modulators which may have utility in the treatment of diabetes. The protein is further characterized in that it possesses optimal activity at neutral pH; its relative activity toward synthetic amino acid-p-nitroanilide substrates is: leucine>>proline, alanine> valine, glycine; its activity is modulated by divalent ions of Co, Zn, Mg, Mn, and Ca; the minimum temperature of inactivation is between 40° C. and 50° C.; its activity is stabilized by ions of Ca; its activity is reduced by phenanthroline, dipyridyl, leuthiol, amastatin, actinonin, and bestatin; and it has at least three glycosylated forms having molecular weights of approximately 165 kD, 155 kD, and 120 kD, respectively. These characteristics are developed in the experimental section, below.

In a second aspect, the invention relates to a method for purifying GTVap and separating glycosylated species thereof, comprising the following steps: (a) extracting the GTVap from at least one source; (b) contacting the resulting GTVap extract with lectin affinity resin to absorb glycosylated GTVap; (c) eluting the glycosylated GTVap from the lectin affinity resin; (d) contacting the eluate from the lectin affinity resin with a chelation chromatography resin which includes a metal ion which interacts simultaneously with the resin and with GTVap; (e) collecting unbound material from the chelation chromatography resin; (f) eluting bound material from the chelation chromatography resin; (g) separately contacting the unbound and the eluted GTVap-containing fractions from the chelation chromatography resin with anion exchange resin; (h) eluting bound GTvap species from the anion exchange resin; and (i) detecting separated GTVap species from the anion exchange resin.

In the claimed method of purifying GTVap and separating glycosylated species thereof, the step of extracting GTVap from at least one biological source of origin is preferably carried out using a mixture of at least one metal ion stabilizer and a detergent. As shown in the experimental section below, the activity of the enzyme decreases with time and in the absence of stabilizing agents. It has now been found that calcium ion, preferably at a concentration of 2 mM, serves as one of a potentially larger number of metal ions which serve to stabilize the activity of the protein. A variety of different detergents may be employed, non-ionic detergents such as Triton X-100 being preferred. The step of contacting the GTVap extract with lectin affinity resin to absorb glycosylated GTVap is carried out using any of a number of commercially available lectins known to those skilled in the art for their ability to absorb glycoproteins. These include Concanavalin A, wheat germ, Helix, *Lens culinaris,* and Limulus lectins. Although wheat germ lectin was employed in this invention, others could have been used. Elution of the glycosylated GTVap from the lectin affinity resin is accomplished using any of a variety of procedures to disrupt the lectin-carbohydrate binding. Examples include use of a competing carbohydrate ligand, and varying the conditions of pH. The chelation chromatography step is conducted by contacting the eluate from the lectin affinity resin with a chelation chromatography resin comprising a metal ion which interacts simultaneously with the resin and with GTVap. There are a number of suitable commercially available chelation chromatography resins. These resins are typically loaded with metal ions which can interact with the protein or glycoprotein being purified, and with the resin. In the present invention, it is preferable to use zinc as the metal ion, as this can interact with the GTVap and with the iminodiacetate resin used. Elution of bound material from the chelation chromatography resin typically is accomplished by adding a chelating agent such as EDTA or by changing the pH. Preferably, conditions which do not alter the intrinsic activity of the enzyme are employed. The step of separately contacting the unbound and the eluted GTVap-containing fractions from the chelation chromatography resin with anion exchange resin can be accomplished using a variety of different supports containing functionally active ligands known to those skilled in the art. The process of this invention preferably uses a resin such as Resource Q which has a high resolution capacity and excellent flow rates when run using fast liquid chromatographic procedures. Elution of bound GTVap species from the anion exchange resin is preferably accomplished by use of an increasing salt gradient, or alternatively, by changing the buffer pH. The step of detecting separated GTVap species from the anion exchange resin is carried out by measuring enzyme activity. The GTVap activity can be detected using any of a number of substrates, including the amino acid-p-nitroanilide derivatives as well as native protein substrates such as insulin. Other substrates could also be employed. This procedure is useful for purification of the enzyme, which in turn permits its further characterization, as well as preparation of antibodies to the enzyme, and identification of modulators of the enzyme's activity.

In a third aspect, the invention relates to a method for identifying modulators of GTVap activity, comprising the following steps: (a) providing GTVap or GTVap-containing material having an assayable amount of enzymatic activity; (b) incubating the GTVap or GTVap-containing material with a test substance to be assayed for ability to modulate GTvap activity; (c) adding a GTVap substrate; (d) monitoring GTVap activity as a function of time; and (e) determining the modulatory effect of the test substance on GTVap.

Regarding the method for identifying modulators of GTVap activity, the step of providing GTVap or GTVap-containing material having an assayable amount of enzymatic activity involves the use of adipose or skeletal muscle tissue, cardiac muscle, cell lines derived from these materials, or recombinant sources known to those skilled in the art. Such tissue would typically be of human or rodent origin, though GTVap also can be derived from other species. Preferably, the human source of the enzyme is used. A recombinant source would be, for instance, insertion of the gene encoding GTVap into a procaryotic or eucaryotic cell line capable of transcribing the inserted gene, resulting in the expression of an enzymatically active GTVap molecule. Such procedures are understood by those skilled in the art. In the step of incubating the GTVap or GTVap-containing material with a test substance to be assayed for ability to modulate GTVap activity the possible test substances would include analogs of known aminopeptidase inhibitors, and synthetic and naturally occurring test substances with no known previous activity. The step of adding a GTVap substrate would typically involve use of a synthetic aminopeptidase substrate such as leucine-p-nitroanilide, or a synthetic or naturally occurring polypeptide substrate in which the N-terminal amino acids could be removed by the particular enzyme. Two examples of suitable polypeptides are insulin and synthetic insulin. The step of monitoring GTVap activity as a function of time is generally carried out by monitoring disappearance of substrate or appearance of the product of enzymatic activity upon the substrate. This is typically accomplished by spectroscopic or chromatographic means, though a wide variety of other techniques have been employed for the purpose, depending on the individual cases. The step of determining the modulatory effect of said test substance on GTVap is carried out by comparing the rate of cleavage of the GTVap substrate in the presence and absence of the test substance.

In a fourth aspect the invention relates to an antibody specific for GTVap, produced using substantially pure GTVap or a fragment thereof.

The antibody specific for GTVap may be produced as follows. Polyclonal antisera is produced against GTVap by injecting intact GTVap or fragments thereof into any of a variety of host animals such as rabbits, mice, goats, and sheep. The antibodies produced in such host animals will be polyclonal in nature, in which case the specific antibodies can be partially purified by procedures known to the art. Furthermore, monoclonal antibodies may be produced by fusion of immunocompetent spleen cells with myeloma cells to yield a hybrid cell line that produces essentially monoclonal immunoglobulin. Under the current state of that art, such animals include mice and rats. The antibodies would find use in the detection and quantitation of GTvap in biological materials. Additionally, such antibodies could be used for the purification of GTvap using immunoaffinity methods known to those skilled in the art.

In a fifth aspect, the invention relates to a naturally occurring inhibitor of GTVap. This inhibitor is associated with and isolatable from GTVap-containing material derived from a biological source; separable from GTVap by lectin affinity chromatography; is of a molecular weight between approximately 10 kD and 20 kD; and inhibits GTVap in the assay of the present invention.

The naturally occurring inhibitor of GTVap can be isolated from GTVap-containing material as explained in the experimental section. In addition to the GTVap-containing material from which this inhibitor was originally isolated, other biological sources may also serve. The inhibitor may be separated from the enzyme by lectin affinity chromatography as well as by other physical separation methods such as gel filtration. In view of the apparent molecular weight of approximately 10–20 kD, this inhibitor is a protein. The naturally occurring inhibitor can be used in the treatment of syndromes of insulin resistance, and to develop drugs to treat such syndromes.

In a sixth aspect the invention relates to a method for preparing proteins and peptides truncated at the amino-terminus, comprising the step of incubating a protein or peptide with GTVap.

Regarding the method for preparing truncated proteins and peptides, the process is carried out by incubating the subject protein under conditions which activate GTVap, i.e., under conditions of neutral pH and in the presence of ions which increase or stabilize the activity of the GTVap. The truncated product is isolated from the reaction by any suitable separating procedure. The method of preparing truncated peptides and proteins is used to derive new pharmacologically active polypeptides.

In a seventh aspect the invention relates to a method for determining GTVap in biological material, comprising the following steps: (a) preparing a specimen of biological material to optimally expose immunoreactive epitopes; (b) incubating this specimen or an extract thereof with GTVap specific antibody; (c) removing unbound antibodies from the specimen; and (d) quantifying antibodies bound to GTVap in the specimen.

Regarding the method for determining GTVap in biological material, the step of preparing a specimen of biological material to optimally expose immunoreactive epitopes is carried out by washing with buffer or treating under more chaotropic conditions which will expose epitopes that are buried in the native conformation of the protein. Such chaotropes would include acetone- or alcohol-containing solutions, SDS, and other denaturants with similar properties. These preparative methods allow detection of either native or denatured GTVap. The step of incubating the specimen or an extract thereof with GTVap specific antibody is carried out in the normal manner, and preferably employs the GTVap1 antibody of the present invention. The GTVap-specific antibody can be labeled directly, with fluorophors, biotin, a radioisotope, or an enzyme such as alkaline phosphatase or horseradish peroxidase. The quantification of antibodies bound to GTVap in the specimen is carried out by identifying the aforementioned labels. Alternatively, bound antibody can be detected using secondary antibodies which are themselves labeled and which will bind specifically to the primary antibody, which is in turn bound to GTVap.

In an eighth aspect the invention relates to an oligonucleotide probe specific for a nucleic acid sequence encoding a segment of GTVap.

Examples of oligonucleotide probes specific for a nucleic acid sequence encoding a segment of GTVap are the following materials, which are shown below in conjunction with the amino acid sequences identified in GTVap, referred to in Table I:
Peptide:
Phe-Ala-Ala-Thr-Gln-Phe-Glu-Pro-Leu-Ala-Ala [SEQ ID NO: 1]
Corresponding "Sense" oligonucleotide:
5' TTY GCN GCN ACN CAR TTY GAR CCN YTN GCN GCN 3'[SEQ ID NO: 3]
Corresponding "Antisense" oligonucleotide:
5' NGC NGC NAR NGG YTC RAA YTG NGT NGC NGC RAA 3'[SEQ ID NO: 4]
Peptide:
Ile-Leu-Gln-Asn-Gln-Ile-Gln-Gln-Gln-Thr-Arg-Thr-Asp-Glu-Gly [SEQ ID NO: 5]
Corresponding "Sense" oligonucleotide:
5' ATH YTN CAR AAY CAR ATH CAR CAR CAR ACN MGN ACN GAY GAR GGN [SEQ ID NO: 6]
Corresponding "Antisense" oligonucleotide:
5' NCC YTC RTC NGT NCK NGT YTG YTG YTG DAT YTG RTT YTG NAR DAT [SEQ ID NO: 7]

In the above sense and antisense oligonucleotides the standard single letter designations are used for the individual bases, and the letter N designates degenerate positions. N is A, T, C, G, or I (inosine); R is A or G; Y is C or T; M is A or C; K is G or T; S is C or G; W is A or T; H is A, C, or T; B is C, G, or T; V is A, C, or G; and D is A, G, or T. Fragments of the above oligonucleotides and additional nucleotide replacements known to those skilled in the art constitute further examples. These oligonucleotides can be used in determining nucleic acids encoding GTVap in biological sources.

In a ninth aspect the invention relates to a method for determining a nucleic acid sequence encoding a segment of GTVap in a biological specimen, comprising the following steps: (a) preparing a biological specimen for analysis of nucleic acid material; (b) incubating nucleic acid material of this biological specimen with an oligonucleotide probe specific for a nucleic acid sequence encoding a segment of GTVap; (c) removing unbound oligonucleotide probe from the nucleic acid material; and (d) determining oligonucleotide probe bound to a nucleic acid sequence encoding a segment of GTVap.

Regarding the method for determining a nucleic acid sequence encoding a segment of GTVap in a biological specimen, the step of preparing a biological specimen for analysis of nucleic acid material is carried out by lysis in detergent, or in an alkaline medium, or through the use of chaotropic agents. This is followed by purification of the DNA or RNA using affinity chromatography (this is useful for mRNA, and uses oligo-dT to purify mRNA), or by centrifugation in CsCl gradients (useful for both DNA and RNA), or by destruction of contaminating material using proteases (to destroy protein) and specific nucleases (to destroy unwanted DNA or RNA). The material can be directly applied to a membrane, separated by gel electrophoresis, or further analysed by restriction digestion before gel electrophoresis. The final material is immobilized on a membrane capable of binding nucleic acid. The steps of incubating nucleic acid material from this biological specimen with an oligonucleotide probe specific for a nucleic acid sequence encoding a segment of GTVap, removing unbound oligonucleotide probe from the nucleic acid material, and determining oligonucleotide probe bound to a nucleic acid sequence encoding a segment of GTVap are carried out in the manner known to those skilled in the art.

The method of treating syndromes of insulin resistance relates to treatment of conditions such as diabetes, obesity, impaired glucose tolerance, hyperinsulinemia, and other conditions associated with hyperinsulinemia such as, but not limited to, Syndrome X, hyperlipidemia, and hypertension. Dosages and times of administration would be in accordance with standard protocols, with the therapeutic aim of lowering blood glucose levels, plasma glucose levels, surrogate markers such as glycated proteins such as hemoglobin $A_{1c}$, and insulin levels, such as, for example, (depending on the specific modulator) orally, transcutaneously, or intranasally, or in an injectable form, subcutaneously, intramuscularly, or intravenously, or by other suitable means, and would have an insulin mimetic activity or insulin enhancing activity. The claimed method can be used alone or in combination with other therapies for treatment of insulin resistance and related syndromes.

Further details will be readily apparent without undue experimentation to those skilled in the art.

Material and Methods

The following list of terms, sources, instruments, etc. is provided to aid the reader in understanding and reproducing the experimental work to be presented below.

Abbreviations and descriptions:

Cellular membrane fractions: PM (plasma membrane), HDM (high density microsomes), and LDM (low density microsomes) are cellular membrane fractions defined by their intrinsic density and sedimentation behavior during centrifugation and by their enrichment of particular enzymes that typify these membranes.

GTVap stands for Glucose Transporter Vesicle aminopeptidase.

GTVap1 refers to rabbit polyclonal antibody produced from the peptide Phe-Ala-Ala-Thr-Gln-Phe-Glu-Pro-Leu-Ala-Ala-(Cys) [SEQ ID NO: 8] that react with the different forms of GTVap.

KRBH buffer is 120 mM NaCl, 4 mM $KH_2PO_4$, 1 mM $CaCl_2$, 10 mM $NaHCO_3$ and 30 mM HEPES, and has a pH of 7.4.

TBS (Tris buffered saline) is 10 mM Tris, 150 mM NaCl, 0.01% Thimerosal, pH 8.0.

TBS-TW is TBS with 0.05% Tween-20.

TES (Tris-EDTA-sucrose) buffer is 20 mM Tris, 1 mM EDTA, 250 mM sucrose, pH 7.5.

SDS-PAGE is sodium dodecyl sulfate—polyacrylamide gel electrophoresis.

Reagents:

Actinonin was obtained from Sigma Chemical Co., St. Louis, Mo.

Amastatin was obtained from Sigma Chemical Co., St. Louis, Mo.

ω-aminohexyl Sepharose 4B was obtained from Sigma Chemical Co., St. Louis, Mo.

Benzamidine was obtained from Sigma Chemical Co., St. Louis, Mo.

Bestatin was obtained from Sigma Chemical Co., St. Louis, Mo.

BSA (bovine serum albumin-Fraction V) was obtained from Sigma Chemical Co., St. Louis, Mo.

Collagenase was obtained from Worthington, Freehold, N.J.

Coomassie blue G-250 and SDS (sodium dodecyl sulfate) were obtained from BioRad, Hercules, Calif.

Cytochalasin B was obtained from Sigma Chemical Co., St. Louis, Mo.

DFP (diisopropylfluorophosphate) was obtained from Aldrich, Milwaukee, Wis.

EDTA is ethylenediaminetetraacetic acid.

HEPES is N-(2-hydroxyethyl)piperazine-N'-(2-ethanesulfonic acid) and is obtained from Sigma Chemical Co., St. Louis Mo.

IAV matrix, Immobilon (AV) membrane was obtained from Millipore Corp., Milford, Mass.

IDAC stands for iminodiacetic acid chelation resin, obtained from Pierce, Rockford, Ill.

Insulin (porcine) was obtained from Eli Lilly, Indianapolis, Ind.

Leupeptin was obtained from Sigma Chemical Co., St. Louis, Mo.

L-leucinethiol was obtained from Sigma Chemical Co., St. Louis, Mo.

Pepstatin A was obtained from Sigma Chemical Co., St. Louis, Mo.

PMSF (phenylmethylsulfonyl fluoride) was obtained from Sigma Chemical Co., St. Louis, Mo.

Problot membranes were obtained from Applied Biosystems, Foster City, Calif.

PVDF membrane is polyvinylidene difluoride, Millipore Corp., Bedford Mass.

Resource Q anion exchange resin contains quaternary ammonium groups on rigid polystyrene/divinylbenzene beads 15 μm in diameter and was obtained from Pharmacia, Piscataway, N.J.

Sinapinic acid (3,5 dimethoxy-4-hydroxycinnamic acid) was obtained from Aldrich, Milwaukee, Wis.

sMBS (m-maleimidobenzoyl-N-hydroxysulfosuccinimide ester) was obtained from Pierce, Rockford, Ill.

Streptavidin was purchased from Zymed Corp., South San Francisco, Calif.

Supelcosil LC-18-DB, 3 μm, 2.1×250 mm columns were obtained from Supelco Corp., Bellefonte, Pa.

TEA (triethylamine) was obtained from Pierce, Rockford, Ill.

TFA (trifluoroacetic acid) was obtained from Applied Biosystems, Foster City, Calif.

Thimerosal is sodium ethyl mercurithiol salicylate, available from Sigma Chemical Co., St. Louis, Mo.

Tris stands for tris hydroxyaminomethane.

Triton X-100 was obtained from Sigma Chemical Co., St. Louis, Mo.

Trypsin (modified sequencing grade, porcine) was obtained from Promega, Madison, Wis.

WGA stands for wheat germ lectin-Sepharose 6 MB, which was obtained from Pharmacia, Piscataway, N.J.

Radiolabeled materials and scintillation fluids $^{125}$I-Protein A (2–10 μCi/μg) was used for Western blot analyses.

All isotopes and scintillation fluids (Aquasol) were from New England Nuclear, Boston, Mass.

General Methods of Peptide synthesis

All peptides including the COOH-terminal 15 amino acid residues of the rat GLUT4 sequence (495–509; [Cys]-Lys-Pro-Ser-Thr-Glu-Leu-Glu-Tyr-Leu-Gly-Pro-Asp-Glu-Asn-Asp [SEQ ID NO: 9]) and fragments thereof (Lys-Pro-Ser-Thr-Glu-Leu-Glu-[Cys] [SEQ ID NO: 10]; Thr-Glu-Leu-Glu-Tyr-Leu-[Cys] [SEQ ID NO: 11]; [Cys]-Gly-Pro-Asp-Glu-Asn-Asp [SEQ ID NO: 12]); the GTVap peptide (Phe-Ala-Ala-Thr-Gln-Phe-Glu-Pro-Leu-Ala-Ala-[Cys] [SEQ ID NO: 8]) and the insulin-derived peptides were synthesized using solid phase methods on the 430A peptide synthesizer previously described in U.S. Pat. No. 5,225,354 of Knowles and Marchesi. All peptides were synthesized with a cysteine residue at the —$NH_2$ or —COOH terminus identified as [Cys] in the sequence and were covalently attached to ω-aminohexyl Sepharose 4B or to a fluorophore for monitoring the proteolytic cleavage of insulin-derived peptides. The peptides were labeled with sulfhydryl-specific fluorescein conjugates. In this procedure a two-fold molar excess of fluorescein-5-maleimide in dimethyl-formamide (40 mg/ml) was added to the peptide (10 mg/ml) in 100 mM sodium phosphate, 5 mM EDTA, pH 7.1 and incubated for 20 hours at room temperature. The resulting peptide-fluorescein conjugate was purified by HPLC chromatography as described by Knowles and Marchesi, U.S. Pat. No. 5,225,354.

Instrumentation

The 477a Protein Sequencer, the 120A Amino acid analyzer and the 430A peptide synthesizer were from Applied Biosystems, Foster City, Calif.

$^{125}$I was measured in a Wallac (LKB) 1272 Clinigamma Counter.

HPLC data acquisition and analysis of the tryptic digests of 155 kD and 165 kD proteins was performed on a Nelson Turbochrome System (Perkin-Elmer Nelson, Norwalk, Conn.)

Mass spectrometry for mass analysis of the synthetic peptides and insulin fragments was performed using a Kratos Maldi 3 laser desorption-time of flight mass spectrometer (LD-TOF-MS), with saturated sinapinic acid, 0.1%TFA, 50% acetonitrile as the matrix.

General method for protein determination

Protein quantities were determined using the bicinchoninic acid method (BCA) as described by the manufacturer (Pierce, Rockford, Ill.)

Immunoaffinity purification of anti-peptide antibodies

The GLUT4 and GTVap anti-peptide antibodies were purified by immunoaffinity absorption prior to their use in Western blots or for the purification of GLUT4 vesicles. For this purpose, the peptide immunogens containing a single cysteine were coupled to Sepharose, as described by the following method. ω-aminohexyl Sepharose 4B resin was washed with 50 mM $Na_2PO_4$, 10 mM EDTA, pH 7.0. The resin was suspended in a 50% slurry and sMBS (2 μmoles/ml resin) added. After 10 minutes at ambient temperature, the derivitized resin was washed in 50 mM $Na_2PO_4$, 10 mM EDTA, pH 7.0, and resuspended to a 50% slurry. The cysteine-containing peptide was added (1–2 mg peptide/ml) and reacted overnight at ambient temperature. The resulting peptide-resin conjugate was washed with 0.1 M acetic acid and then 50 mM $Na_2PO_4$, 10 mM EDTA, pH 7.0 prior to use.

For immunoaffinity purification, polyclonal antisera to the individual peptides were diluted 1:1 with 100 mM $NaH_2PO_4$, 150 mM NaCl, pH 7.5 and applied to the corresponding peptide-resin. Following a brief wash with the above buffer, the bound affinity-purified antibody was eluted with 0.1M acetic acid and the pH immediately adjusted to pH 8.0 with 1.0M Tris base. The purified antibody was dialyzed against and stored in 0.4M sodium borate pH 8.0 containing 0.5% sodium azide.

Western blot analysis

Prior to Western blot analysis, proteins were electrophoresed on SDS-PAGE gels (Laemmli, Nature, 277, 680–685, 1970) and transferred to PVDF or Problot membranes by the method of Tobin, et al, PNAS, 76, 4350–4354, 1979. For Western blot analysis of GLUT4 and GTVap, rabbit anti-GLUT4 antibody, immunoaffinity-purified as above, was used at a 1:5000 dilution (1 μg/5 ml); GTVap affinity purified antibody was used at 1:1000 (1 μg/ml). For detection of the primary antibody, both Protein A $^{125}$I (1 μCi/ml) and goat anti-rabbit alkaline phosphatase (1:10,000; Promega) were used sequentially. The immunoreactive bands were identified by the colored alkaline phosphatase reaction product and/or by autoradiography of the $^{125}$I-Protein A, and were quantified by $^{125}$I-Protein A counting on a LKB 1272 Clinigamma counter.

Experimental and Results:

Generation of GLUT4 specific antibodies

GLUT4 rabbit polyclonal antibody was produced using a synthetic peptide corresponding to the COOH-terminal 15 amino acid residues of the rat-GLUT4 sequence, i.e., residues 495–509, [Cys]-Lys-Pro-Ser-Thr-Glu-Leu-Glu-Tyr-Leu-Gly-Pro-Asp-Glu-Asn-Asp [SEQ ID NO: 9]. The antibody specificity for GLUT4 was enhanced by absorbing the polyclonal sera with 3 peptides (Lys-Pro-Ser-Thr-Glu-Leu-Glu-[Cys] [SEQ ID NO: 10]; Thr-Glu-Leu-Glu-Tyr-Leu-[Cys] [SEQ ID NO: 11]; [Cys]-Gly-Pro-Asp-Glu-Asn-Asp [SEQ ID NO: 12] covalently attached to ω-aminohexyl Sepharose 4B using the heterobifunctional reagent SMBS. The nonabsorbed GLUT4 specific antibody was purified on a 495–509 peptide column and then on Protein-A Sepharose. The resulting highly purified and specific GLUT4 antibody was used for Western blotting at a 1:5000 dilution (1 μg protein/5 ml diluent).

Preparation and isolation of rat adipocytes

Epididymal fat pads from 125 g Sprague-Dawley rats were removed and immediately placed in KRBH buffer containing 1% BSA, 2.5 mM glucose and 200 nM adenosine. The fat was minced, collagenase was added to 3 mg/ml, and the mixture was incubated at 37° C. for 45 minutes with shaking. The dissociated adipocytes were filtered through a 250 micron nylon screen and washed 3 times (using mild centrifugation) with KRBH containing 1% BSA and 200 nM adenosine. The cells were resuspended in the wash buffer containing 3% BSA.

Fractionation of rat adipocytes

The membrane fractions PM, HDM and LDM were prepared generally according to Simpson et. al., Biochimica et Biophysica Acta, 763, 393–407 (1983). Isolated adipocytes were homogenized in a chilled Wheaton 55 ml teflon pestle homogenizer for ten strokes. The fat layer was removed following a 10,000×g centrifugation and the remaining material was rehomogenized. The PM fraction was pelleted at 16,000×g and the supernatant was recentrifuged to remove any additional PM. The PM were resuspended and rehomogenized then purified away from DNA and mitochondrial organelles by ultracentrifugation through a 1.12M sucrose cushion at 96,000×g. The PM were collected from the interphase of the sucrose cushion. The HDM were pelleted from the initial supernatant at 48,000×g and the resulting supernatant was recentrifuged to remove any remaining HDM. The LDM were collected on a 1.12M sucrose cushion from the HDM supernatant by centrifugation of at 212,000×g. The LDM were collected from the sucrose interphase and this step was repeated three times with LDM pooled from additional tubes to concentrate the LDM and to remove any contaminating cytosolic proteins.

Immunopurification of the GLUT4 vesicles

Purified GLUT4 specific antibody prepared as above was biotinylated using NHS-biotin in 50 mM $NaHCO_3$, pH 8.2, for 30 minutes at room temperature. Following dialysis against 20 mM Tris, 1 mM EDTA, pH 8.0, the active biotinylated antibody was recovered by affinity purification on [Cys]-Lys-Pro-Ser-Thr-Glu-Leu-Glu-Tyr-Leu-Gly-Pro-Asp-Glu-Asn-Asp [SEQ ID NO: 9]) covalently bound to aminohexyl-Sepharose CL-4B as described above.

Immobilon Affinity Membranes (IAV, 1 cm$^2$) were saturated for 6 hours at room temperature and then overnight at 4° C. with 500 μg of streptavidin in 0.5M $KH_2PO_4$, pH 7.5. Residual sites were capped with 0.44M glutamic acid (6 hours, room temperature) and the membranes were washed. Biotinylated anti-GLUT4 antibody (50 μg/cm$^2$) described above was added in 100 mM boric acid, 150 mM NaCl, 1 mM EDTA, pH 7.5, and contact was maintained for 6 hours at room temperature. The resulting antibody-derivitized IAV matrix was washed 3 times (20 minutes/wash) in TBS, 0.1% Tween-20, and then transferred into TES. Control IAV matrix was prepared with streptavidin and capped with glutamic acid.

LDM were added to the GLUT4 or control IAV matrices. Typically, the LDM's from 2.4 rats were added to each 1 cm$^2$ of matrix, and incubated overnight at 4° C. in TES containing 150 mM NaCl, and subsequently washed 3× in the same buffer. Unbound vesicles were recovered by centrifugation at 212,000×g. Bound vesicular protein was recovered by eluting the matrices with 1.0% SDS in 10 mM Tris-HCL, pH 7.4, or in 0.1% Triton X-100 in 20 mM Tris, 1 mM EDTA, pH 7.4. GLUT4 vesicle proteins were frozen in liquid $N_2$ and stored at −80° C. until further use.

For protein analysis, equal volumes of purified GLUT4 vesicles and controls, along with equal protein loads of recovered unbound LDM vesicles were lyophilized and loaded onto 4–20% SDS-PAGE gels, transferred to PVDF membranes, and stained with Coomassie Blue R-250. A protein having a molecular weight of approximately 165 kD was characterized as being specific to the GLUT4 vesicles and was partially to fully depleted from the unbound fraction.

FIG. 1 shows qualitatively by Western Blot autoradiography that the immunoaffinity absorption using GLUT4 antibody-derivitized IAV matrix results in a significant enrichment of GLUT4 vesicles compared to IAV matrix lacking the GLUT4 antibody. Quantitation of the $^{125}$I Protein A indicated an 8-fold enrichment of GLUT4 in the immunoaffinity-purified vesicles. The immunoaffinity-purified GLUT4 vesicle proteins can be solubilized using 0.1% Triton X-100 or low concentrations (<1%) of SDS, leaving the antibody attached to the covalently bound streptavidin, to yield a protein composition much simpler than the total LDM fraction.

Figure 2:
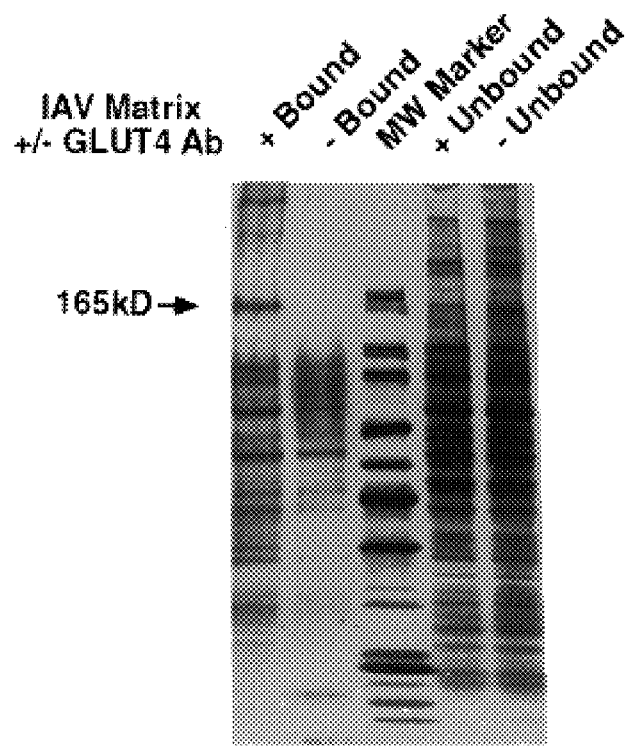
FIG. 2 is a protein stain of immunoaffinity-purified GLUT4 vesicles.

FIG. 2 shows that Coomassie blue staining of the GLUT4 vesicle-associated proteins following SDS-PAGE reveals 165 kD and 155 kD proteins which are uniquely associated with GLUT4 vesicles and which are not found in proteins absorbed onto the IAV matrix lacking the GLUT4 antibodies. Both the 165 kD and 155 kD proteins are depleted from the LDM following adsorption with GLUT4 IAV matrix, but are not depleted after adsorption on the control matrix.

Purification and sequence analysis of 165 kD and 155 kD proteins

GLUT4 vesicle proteins were electrophoretically separated on 20 cm, 7–15% acrylamide, SDS-PAGE gels and transferred to Problot membranes. The 165 kD and 155 kD proteins were identified by Coomassie blue staining. Initial attempts at direct $NH_2$ terminal sequencing from the Problot membrane indicated that the $NH_2$-terminus was blocked. In subsequent experiments the 165 kD and 155 kD proteins were separated and identified as above, and were then digested with trypsin (30:1; substrate/enzyme) according to Fernandez et al., Analyt. Biochem., 201, 255–264 (1992). The resulting peptide products were separated on a Supelcosil LC-18-DB, 3 μm, 2.1×250 mm column using a 3-hour linear gradient of 0.1% TFA to 0.1%TFA, 70% acetonitrile. The effluent was monitored at 215 nm and selected peaks were subjected to sequencing using an ABI 477a Protein Sequencer operated in the gas phase with an on-line 120A Analyzer and PE Nelson Turbochrome Software.

Figure 3:
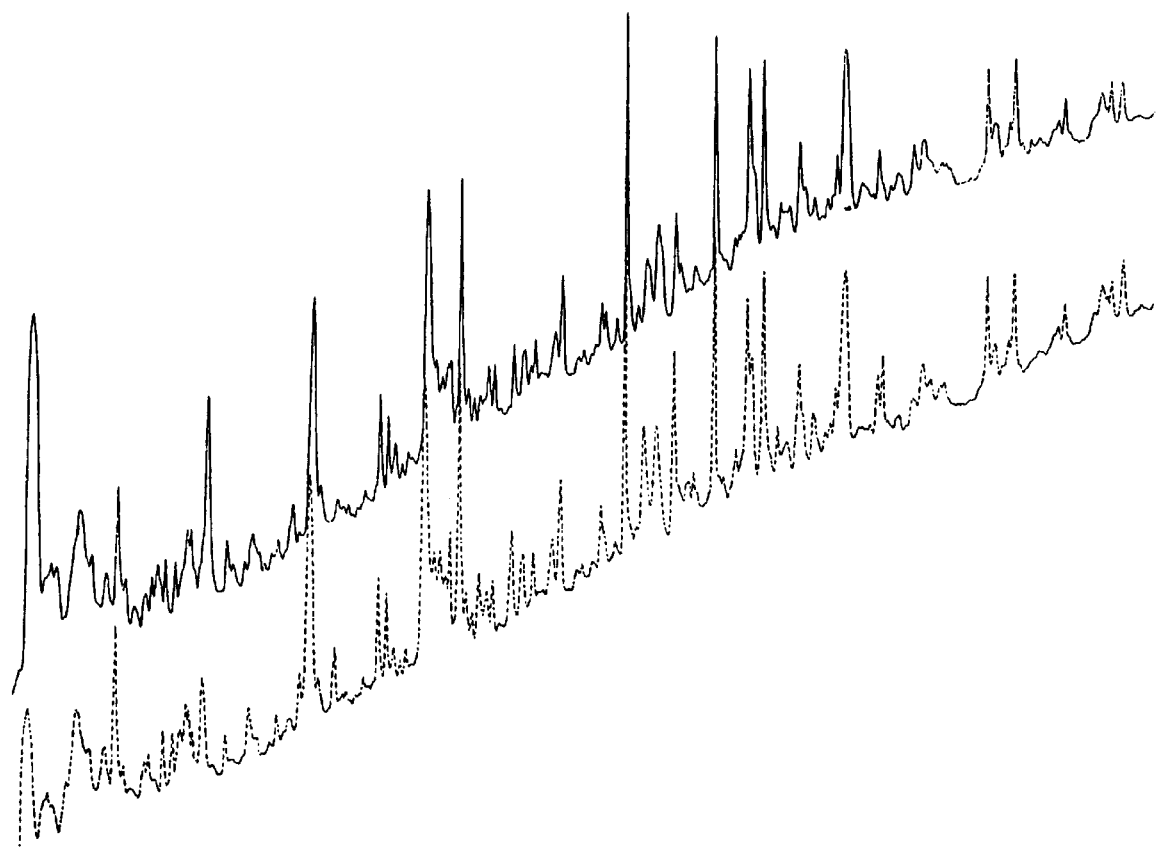
FIG. 3 shows the HPLC profiles of tryptic digests of 165 kD (upper trace) and 155 kD (lower trace) GLUT4 vesicle proteins.

FIG. 3 shows HPLC separations of the tryptic fragments and indicates significant similarity between the two proteins. Selected peptides of moderate hydrophobicity and strong UV absorbance were sequenced. The sequences obtained are shown in Table 1. Both peptides were sequenced from the 165 kD and 155 kD forms and were identical, constituting further evidence of the similarity between these two proteins.

Identification of GLUT4 vesicle protein 165 kDa as an aminopeptidase

The primary sequence obtained was used to search DNA databases including GenBank, EMBL, Nucleic, and GeneSeq, and the Protein databases PIR, PatchX, and SwisProt. One peptide was found to have 100% homology with a tryptic fragment of a serum aminopeptidase of placental origin in the GeneSeq database. See Table 1.

TABLE 1

Summary of Sequence Data for GTV-165 and GTV-155

| Fragment No. | Sequence | Identity |
|---|---|---|
| 1 | Phe-Ala-Ala-Thr-Gln-Phe-Glu-Pro-Leu-Ala-Ala-arg* [SEQ ID NO: 13] | None found |
| 2 | Ile-<u>Leu-Gln-Asn-Gln-Ile-Gln-Gln-Gln-Thr-Arg-Thr-Asp-Glu-Gly-thr-Pro</u>-asn-Met* [SEQ ID NO: 14] | Leucine Amino Peptidase (found in GeneSeq patent database) Accession #GSP:R28142; EP 0 535 241 A1 |

Underlined residues of fragment #1 were used to produce high titered rabbit polyclonal antisera.
Underlined residues of fragment #2 had 100% homology with a previously identified placental leucine aminopeptidase (PLAP).
*Designates same sequence found in both GTV-165 and GTV-155
Residues in lower case letters denote less than full confidence, and are assigned the designation Xaa in the claims.

The peptide Phe-Ala-Ala-Thr-Gln-Phe-Glu-Pro-Leu-Ala-Ala-[Cys] [SEQ ID NO: 8] was used to produce rabbit polyclonal antibodies which were subsequently affinity purified as described above. These antibodies are referred to as GTVap1 and were used at a 1:500 dilution for Western blot analysis.

Figure 4:
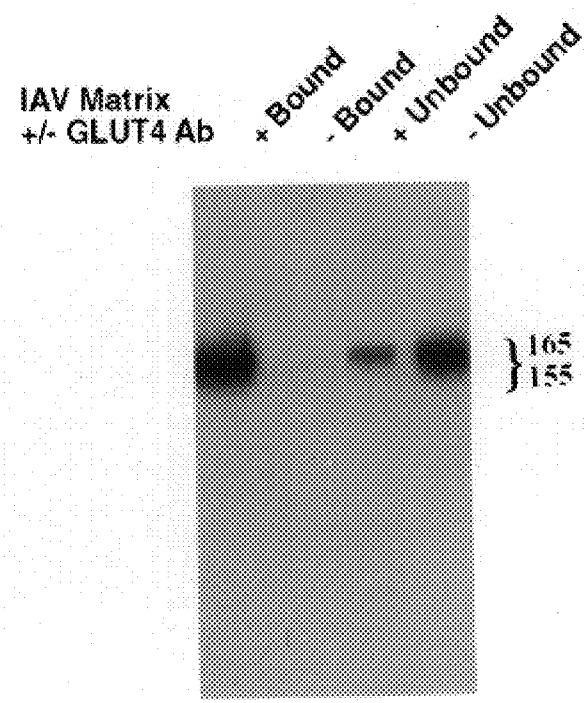
FIG. 4 is a Western blot showing the enrichment of the 165 kD protein in GLUT4 vesicles.

FIG. 4 shows the affinity purified GTVap1 antibodies in Western blot analysis are specific for the 165 kD and 155 kD proteins on the GLUT4 vesicles and also react with a 120 kD protein which is less abundant than the former two. Relative to the controls, the purified GLUT4 vesicles are significantly enriched in the immunoreactive 165 kD and 155 kD proteins, as measured by Western blot. Quantitation of the $^{125}$I Protein A indicated an 18-fold enrichment of the 165 kD and 155 kD proteins on the immunoaffinity-purified vesicles.

In order to show identity of the 165 kD and 155 kD proteins by removal of the oligosaccharide side chains, LDM was treated with N-glycosidase F. Purified LDM was solubilized in 0.5% SDS and then buffered in 25 mM Hepes, 10 mM EDTA, 1.7% β-octylglucoside, pH 7.5 before being digested with 1 unit of N-Glycosidase F (PNGase F) per sample for 12 or 24 hours at 37° C. Controls (samples lacking the glycosidase) were included for each condition.

Figure 5:
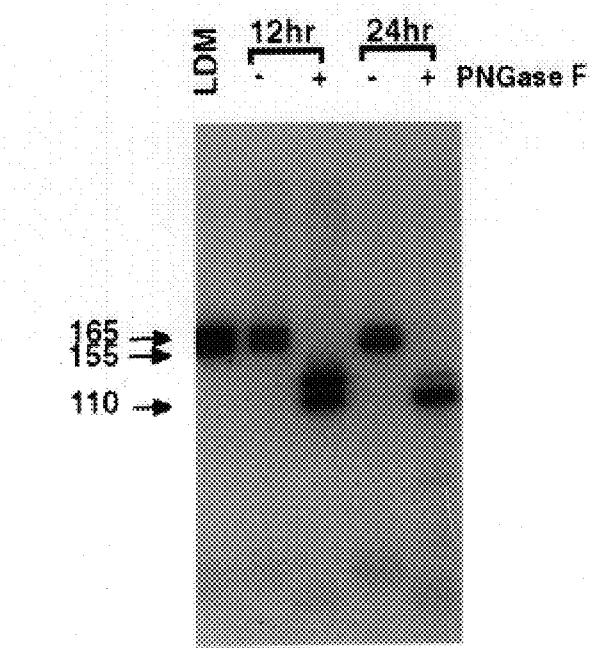
FIG. 5 is a Western blot of the LDM 165 kD and 155 kD proteins following treatment with N-Glycosidase F.

FIG. 5 indicates that treatment of LDM with N-glycosidase F results in the conversion of both the 165 kD and 155 kD immunoreactive proteins to a single immunoreactive protein of 110 kD. This suggests that both forms are identical at the protein level with differences existing in the number and/or length of oligosaccharide side chains of the glycosylated 165 kD and 155 kD forms.

The 165 kD and 155 kD proteins have sequence homology to a previously identified aminopeptidase, and GLUT4 vesicles are enriched in aminopeptidase activity As indicated in Table 1, the peptide sequence of fragment #2 had 100% homology with a previously reported plasma aminopeptidase of placental origin (Tsujimoto et al. EPA Pub. # EP 0 535 241 A1).

Figure 6:
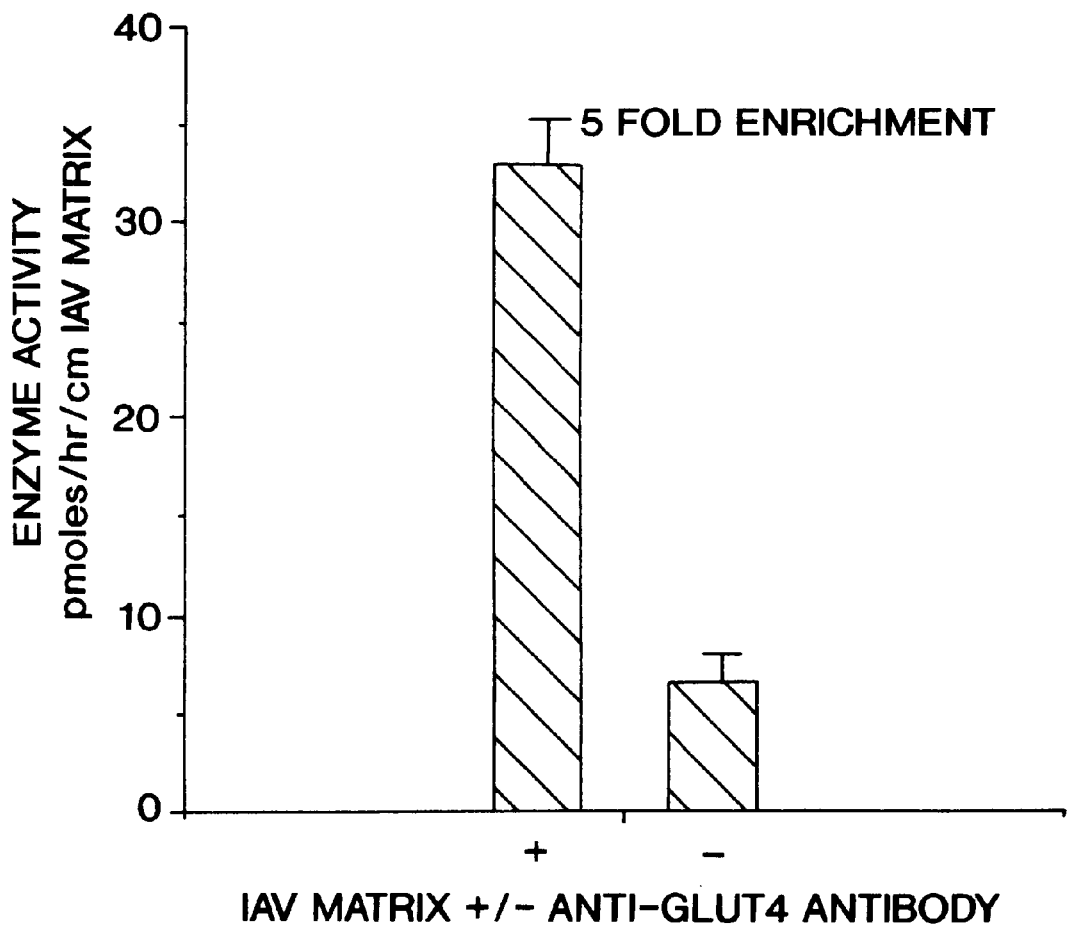
FIG. 6 is a graph showing the quantitative enrichment of aminopeptidase activity in GLUT4 vesicles.

The synthetic substrate leucine-p-nitroanilide was used to confirm that aminopeptidase activity was co-purified with GLUT4 vesicles. Immunoaffinity purified GLUT4 vesicles or vesicles bound non-specifically to the control IAV membranes were extracted with 20 mM Tris, 0.1% Triton X-100, pH 7.5. Equal volumes of extract from the two matrices were assayed for aminopeptidase activity using 1.6 mM leu-p-nitroanilide. The results, shown in FIG. 6, indicate that GLUT4 vesicles contain 5-fold more aminopeptidase activity that the control IAV matrix. Therefore, aminopeptidase activity co-purifies with GLUT4 vesicles.

Throughout this application the term Glucose Transporter Vesicle aminopeptidase or GTVap is used to designate the aminopeptidases associated with GLUT4 vesicles.

Identification of GTVaps in PM and HDM membranes

Figure 7:
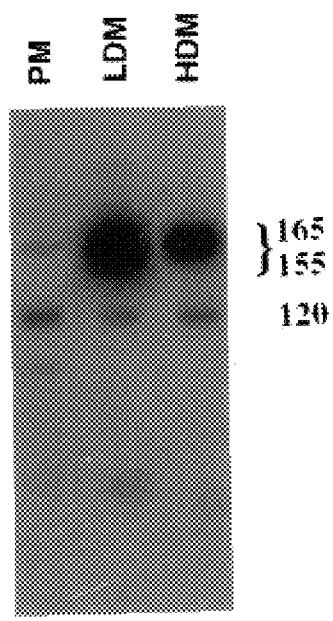
FIG. 7 is a Western blot of the 165 kD protein in rat adipocyte membrane fractions.

As shown in FIG. 7, the GTVaps are also found in PM and HDM fractions by Western blot analysis using the GTVap1 antibody. The GTVap-165 and GTVap-155 are the predominant forms in the HDM and LDM, whereas in the PM these GTVap's are much less abundant.

Figure 8:
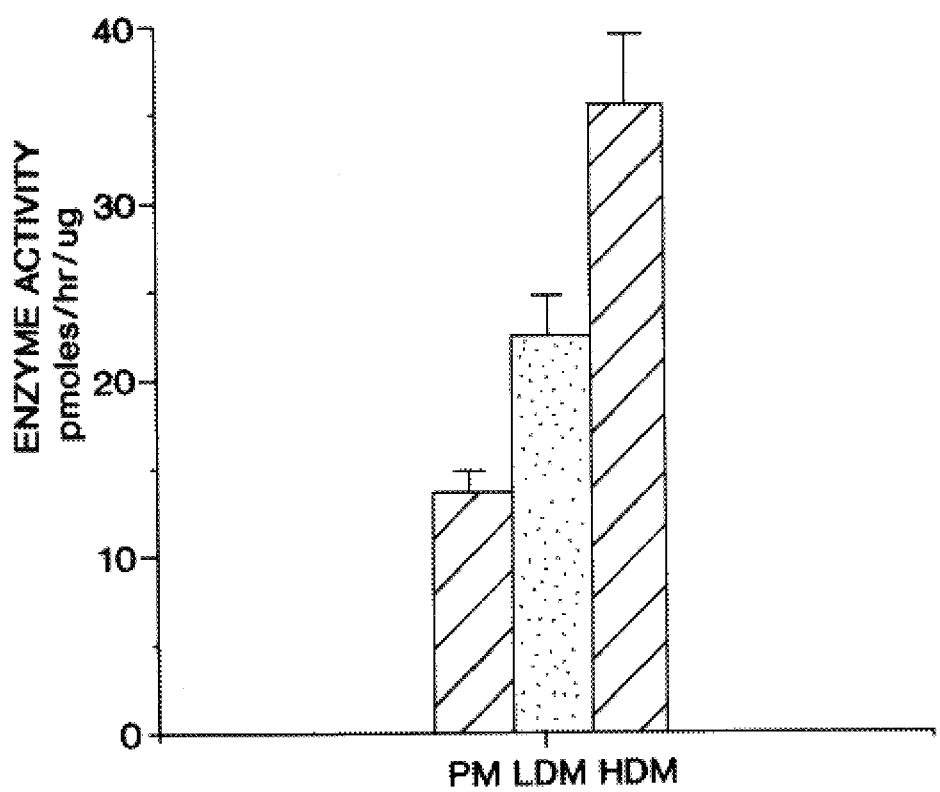
FIG. 8 is the GTVap enzyme activity in rat adipocyte membrane fractions.

General methods for the extraction of and assay of GTVaps from PM, LDM, and HDM membranes The GTVaps can be maximally extracted (>95%) from the LDM, HDM, and PM membranous compartments using low concentrations of detergents. Unless otherwise indicated, the GTVaps were solubilized from GLUT4 vesicles, LDM, HDM, and PM using 0.1% Triton-X 100 in 20 mM Tris, pH 7.5 at 4° C. for 15 minutes. The insoluble material was pelleted at 20,000× g for 20 minutes and discarded. The enzyme extract (10–20 µg protein) was assayed using 1.6 mM leucine-p-nitroanilide in 20 mM Tris-HCl, 0.1% Triton X-100, pH 7.5 in 250 µl volume at 37° C. The UV absorbance of the p-nitroanilide product was measured at 405 nm and quantified by comparison to p-nitroanilide standards. The results are reported as pmoles p-nitroanilide produced per µg protein/hour at 37° C. unless otherwise noted. Alternatively, the results are presented as change in OD at 405 nm if the protein was too low to determine (eg column fractions) or a relative comparison was being made. As shown in FIG. 8, the PM, LDM, and HDM contain GTVap activity.

Although the GLUT4 vesicles were shown initially to have aminopeptidase activity, it was necessary to confirm that the 165 kD and 155 kD proteins were indeed the aminopeptidases. Due to the limited amount of protein obtainable from the purified GLUT4 vesicles or LDM, it was necessary to characterize and purify the enzyme from the HDM.

Characterization of the activity of the GTVap enzyme

In order to characterize the relative reactivities of GTvap to different amino acid-p-nitroanilide substrates, a HDM extract was prepared as described above and incubated with each substrate at a concentration of 1.6 mM as described above. As shown in Table 2, the relative activity of GTVap to the synthetic amino acid-p-nitroanilide substrates are leucine>>proline, alanine>valine, glycine.

Figure 9:
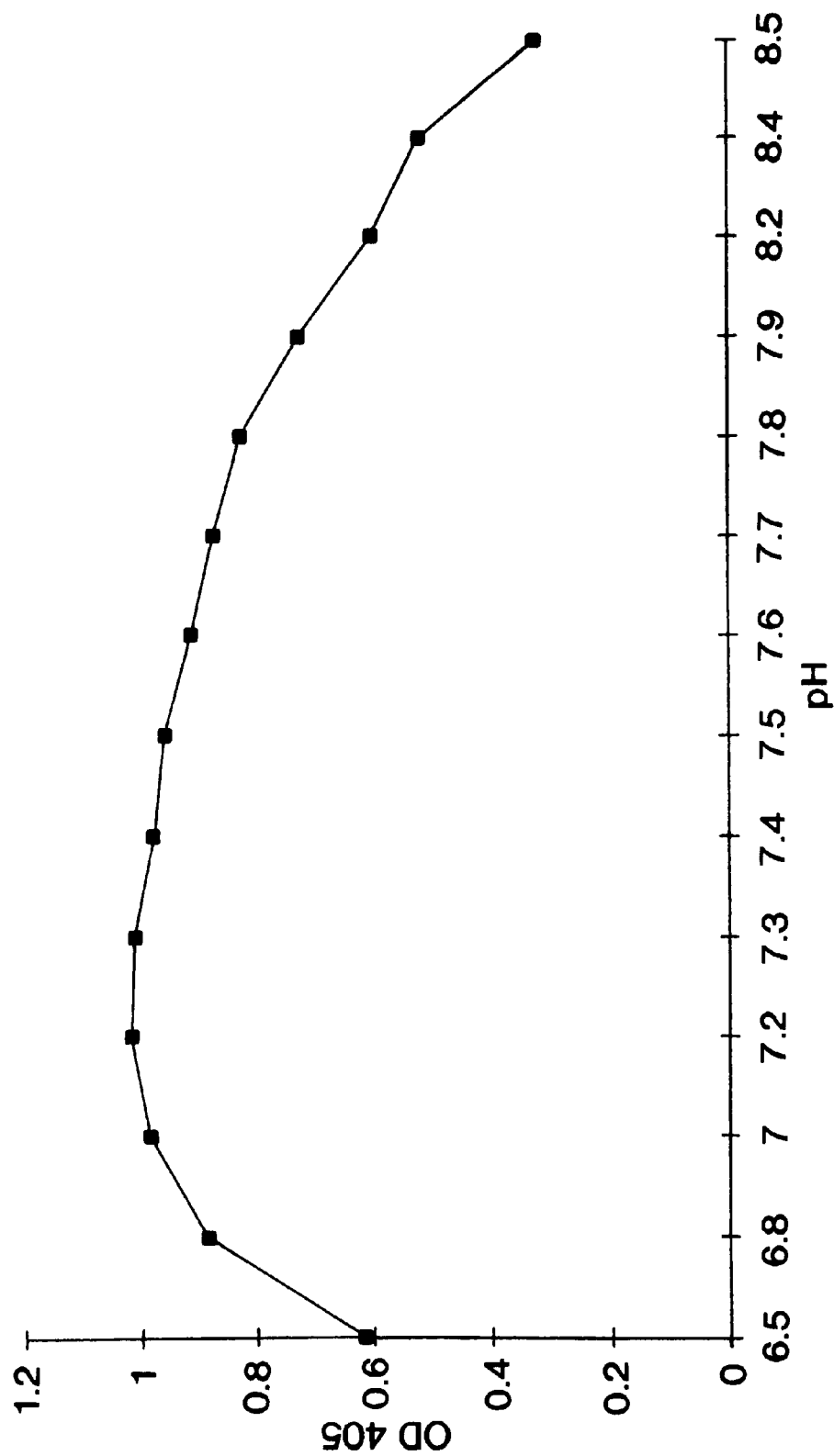
FIG. 9 is a graph showing the pH optimum of GTVap.

In order to determine the optimal pH of the GTVap activity, an HDM extract was prepared as above and was diluted 1:9 into 100 mM Tris base, 0.1% Triton-X 100 which had been previously adjusted to the indicated pH values with HCl. Following incubation for 15 minutes, the leucine-p-nitroanilide substrate was added and the enzyme activity determined as above. The results shown in FIG. 9. indicate that the enzyme has a broad neutral pH optimum.

TABLE 2

Relative activity of GTVap with various amino acid-p-nitroanilide substrates

| Amino acid-p-nitroanilide | pmoles/µg protein/hr |
| --- | --- |
| leucine | 29.5 |
| proline | 3.5 |
| alanine | 3.3 |
| valine | 0.92 |
| glycine | 0.77 |

Figure 10:
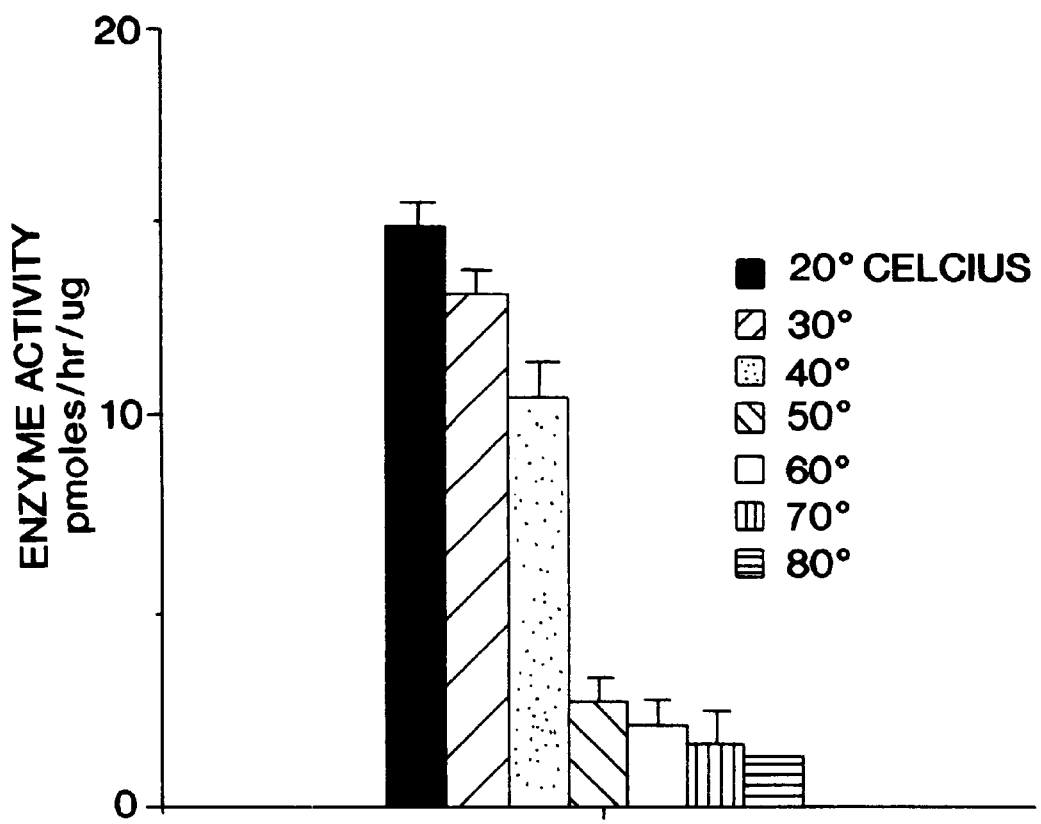
FIG. 10 is a graph showing the temperature stability of GTVap.

In order to determine the temperature stability of GTVap, HDM extracts were incubated at various temperatures for 20 minutes prior to enzyme analysis as described above. The results shown in FIG. 10 indicate a temperature-dependent inactivation with a 25% reduction in activity between 20° C. and 40° C. Between 40° C. and 50° C. there is a further major drop in activity, resulting in a 75% inhibition compared to the 20° C. incubation.

Figure 11:
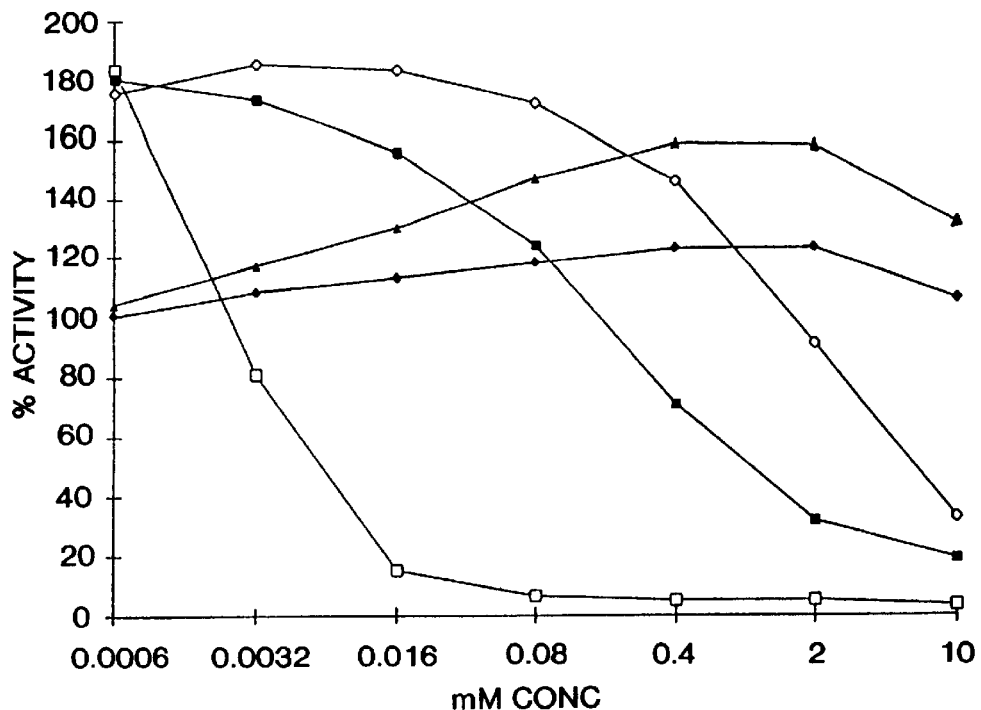
FIG. 11 is a graph of the effect of various ions on GTVap activity: Co (solid squares); Zn (open squares); Mg (solid diamonds); Mn (open diamonds); Ca (solid triangles)

The known aminopeptidases require bound ions for the optimal stabilization of structure and for maximal enzymatic activity. To explore the ion requirements for GTVap, Triton-X extracts of HDM were incubated with various ions for 15 minutes at 37° C. before the addition of the leu-p-nitroanilide substrate. The results, shown in FIG. 11, demonstrate that particular ions can both activate and inhibit the enzyme activity. It is also evident that the enzyme has significant activity (approx. 55% of maximal activity) without the addition of divalent cations. Zinc, cobalt and manganese optimally activate at µmolar concentrations and inhibit at mmolar concentrations. Calcium and magnesium also partially activate, but at high µmolar to mmolar ion concentrations. The ions of lithium and potassium have no effect on enzyme activity between 1M and 10 mM.

Figure 12:
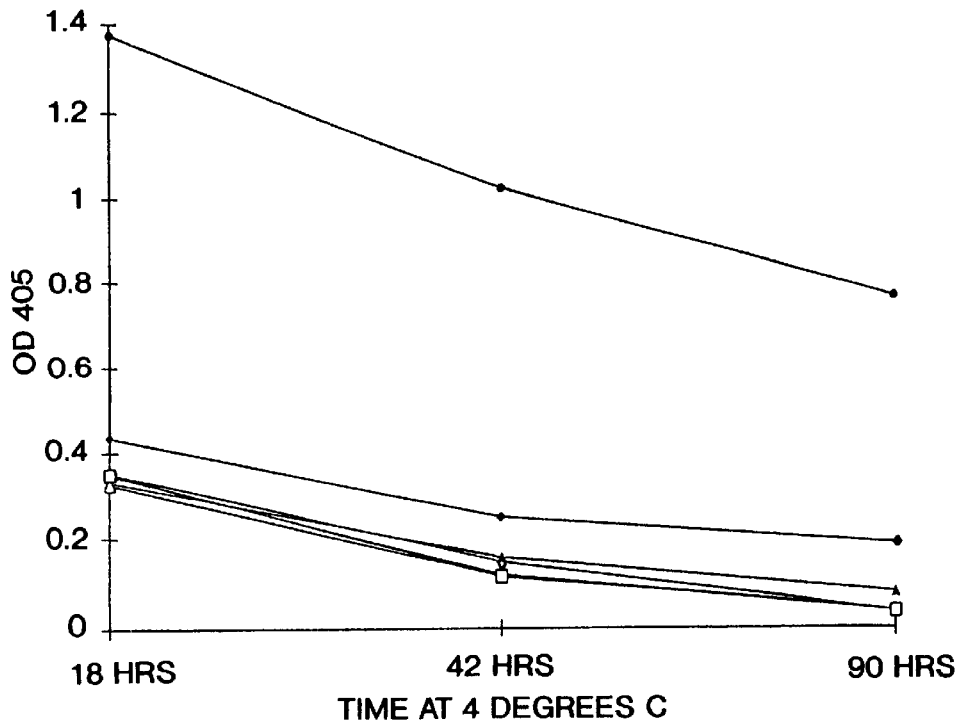
FIG. 12 is a graph of the ion enhancement of GTVap stability: control (open diamonds); 2 mM Mg (solid triangles); 0.02 mM Mn (open triangles); 2 mM Ca (solid circles); 1 $\mu$M Zn (solid squares); 1 $\mu$M Co (open squares); 0.2 mM DTT (solid diamonds)

It was evident during the initial investigations of GTVap that the Triton-X 100 extracts lose enzyme activity over time at 4° C. An attempt was made to stabilize enzyme activity by adding specific ions that were previously shown to activate the enzyme. Immediately following the routine extraction of HDM the extract was diluted into 20 mM Tris-HCl, pH 7.5 containing the ions or DTT at concentrations that were previously shown to enhance enzyme activity. After various times at 4° C. aliquots were removed and GTVap activity determined. The results, shown in FIG. 12, indicate that calcium stabilizes the enzyme activity against the time dependent inactivation. Zinc, cobalt and manganese, which were previously shown to increase activity, do not stabilize the enzyme.

A number of protease inhibitors were studied to examine their inhibitory effects on GTVap. The methods of enzyme determination have been described above with the exception that various concentrations of the inhibitors were added to HDM enzyme extracts 15 minutes prior to the addition of 10× leu-p-nitroanilide substrate. The data is presented relative to the inhibitor-free control which has 100% activity. The following inhibitors, with the maximal concentration tested being shown in parentheses, had no effect on GTVap activity using the leucine-p-nitroanilide substrate: diisopropylfluorophosphate (5 mM), PMSF (1 mM), benzamidine (10 mM), leupeptin (5 mM), EDTA (5 mM).

Figure 13:
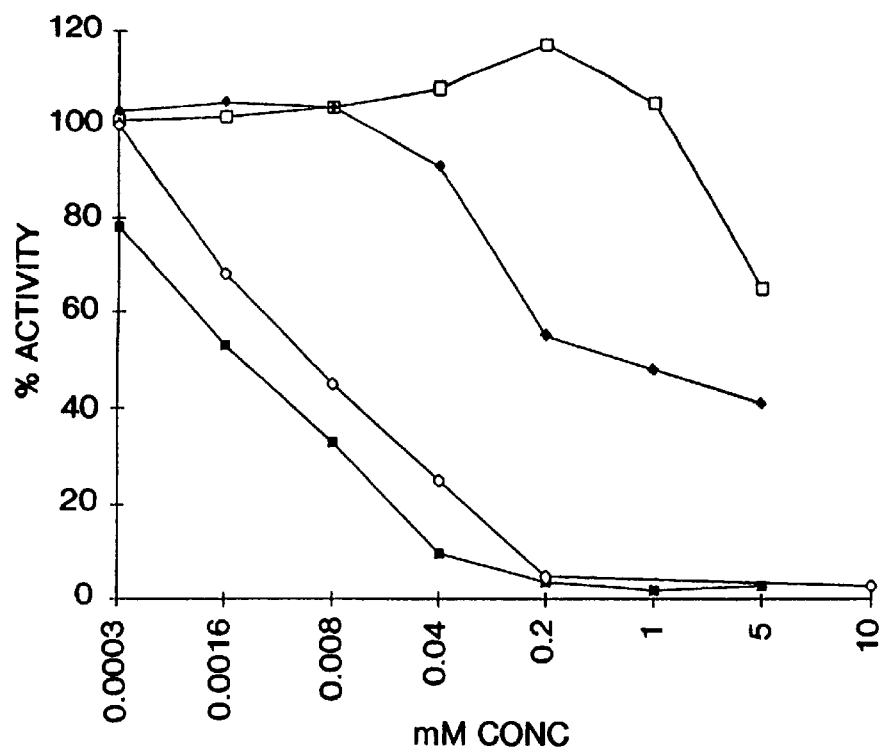
FIG. 13 is a graph of showing the effects of various protease inhibitors on GTVap activity: phenanthroline (solid squares); DTT (open squares); LLPAC (solid diamonds); dipyridyl (open diamonds)

Two zinc chelators, phenanthroline and dipyridyl, were found to be >98% inhibitory at >0.2 mM, as shown in FIG. 13.

Leu-Leu-Phe-chloromethyl ketone (LLPAC), a known inhibitor of calpain, has an GTVap $IC_{50}$ of 1 mM. Dithiothreitol (DTT) has a 30% inhibition at 5 mM but increases enzyme activity 20% at 0.2 mM.

Figure 14:
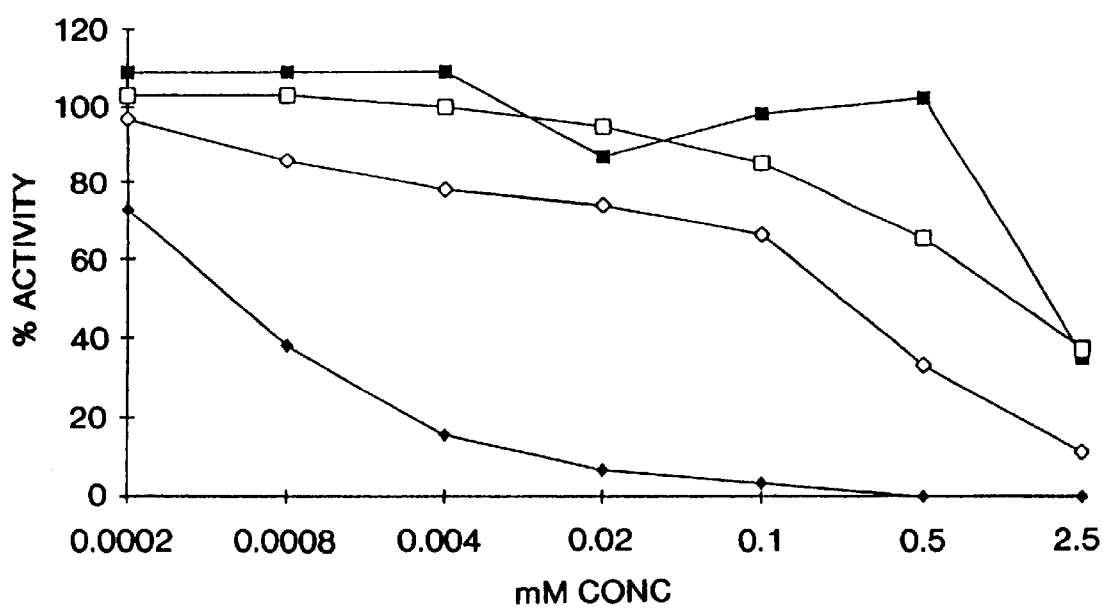
FIG. 14 is a graph of the effects of various aminopeptidase inhibitors on GTVap activity: bestatin (solid squares); actinonin (open squares); leuthiol (solid diamonds); amastatin (open diamonds)

A number of previously identified aminopeptidase inhibitors were tested on GTVap. The most effective inhibitor was leuthiol with an $IC_{50}$ of 2 μM. Amastatin had an $IC_{50}$ of 0.35 mM and bestatin and actinonin had $IC_{50}$'s of >1 mM, as shown in FIG. 14.

Purification of GTVap 165. 155 and 120 from HDM's

The strategy for the purification of the GTVap enzymes was formulated based on the relatively rapid time-dependent inactivation of the enzyme. The purification scheme employs two affinity purifications (WGA and IDAC) followed by an anion exchange chromatographic separation. Calcium ions were used to maintain optimal stability whenever possible.

Purified HDM at a concentration of 1 mg/ml was solubilized in 20 mM Tris-HCl, 0.1% Triton X-100 containing 2 mM CaCl2, 150 μM PMSF, 1 mM DFP, 1 mM benzamidine, 2 μM leupeptin, and 1 μM pepstatin A. This extraction was found to solubilize 96% of the total aminopeptidase activity and 77% of the total protein of HDM fraction. The unsolubilized membrane was pelleted at 48,000×g for 20 minutes and discarded. The solubilized extract was batch incubated with wheat germ agglutinin (WGA)-Sepharose. In particular, one ml of packed wheat germ lectin-Sepharose 6 MB resin, referred to as WGA, was added per 10 mg HDM of protein and rotated overnight at 4° C. The resin was washed with the above buffer without $CaCl_2$ and eluted with 5.0 ml of 0.5M N-acetylglucosamine. Approximately 93% of the total aminopeptidase activity was bound and could be eluted from the WGA column using 0.5M N-acetylglucosamine. The WGA purified fraction could be applied directly to the anion exchange Resource Q column. Typically, the entire WGA purified fraction was applied to a 1 ml Resource Q anion exchange resin column at 4° C. A linear gradient of 0–0.5 M NaCl in 20 mM Tris, 0.1% Triton X-100, pH 7.8 at 4° C. was used for elution. All fractions were assayed for aminopeptidase activity and for Western blot reactivity to the GTVap1 antibody.

Figure 15A:
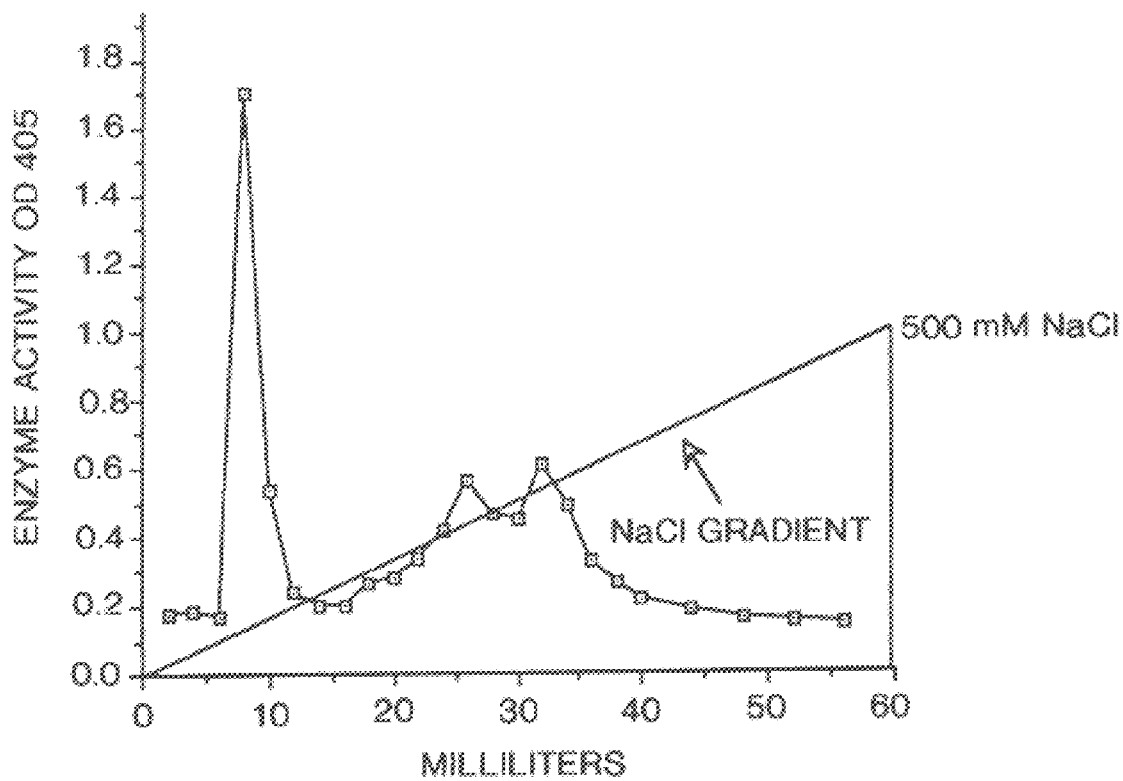
FIG. 15a is a graph of GTVap activity following an anion exchange chromatographic separation of WGA-purified GTVap.
Figure 15B:
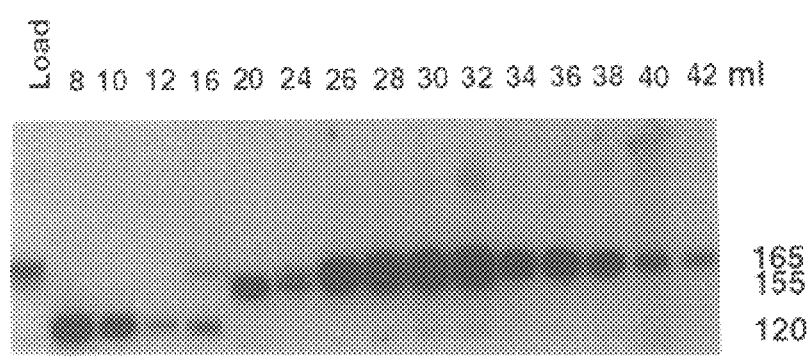
FIG. 15b is a Western blot of GTVap-120, 155 and 165 following an anion exchange chromatographic separation of WGA-purified GTVap.

As shown by FIGS. 15a and 15b, this ion exchange method separates the 120 kD immunoreactive protein from the GTVap-155 and GTV-165 kD forms. The Resource Q Western blot profile using GTVap1 antibody identification of the 120 kD protein and GTVap-155 kD and 165 kD proteins shows excellent correlation with aminopeptidase activity. The sharp early eluting peak from the Resource Q column is the GTVap-120 with the later-eluting broad peak being first the GTVap-155, followed closely by GTVap-165.

Alternatively, the WGA purified fraction also could be applied directly to an iminodiacetic acid column preloaded with zinc. In particular, the WGA purified fraction was immediately passed down a 0.5 ml iminodiacetic acid chelation (IDAC) column previously loaded with 10 mM $ZnSO_4$ in 20 mM Tris, 0.1% Triton X-100, pH 7.5, according to the manufacturer's recommendation. After the application of WGA eluate, the column was washed with 10 column volumes of 20 mM Tris, 0.1% Triton X-100, pH 7.5. The column was then eluted with 10 mM EDTA in 20 mM Tris, 0.1% Triton X-100, pH 7.5. Approximately 93% of the aminopeptidase activity was bound to the IDAC and could be eluted with 10 mM EDTA.

Figure 16:
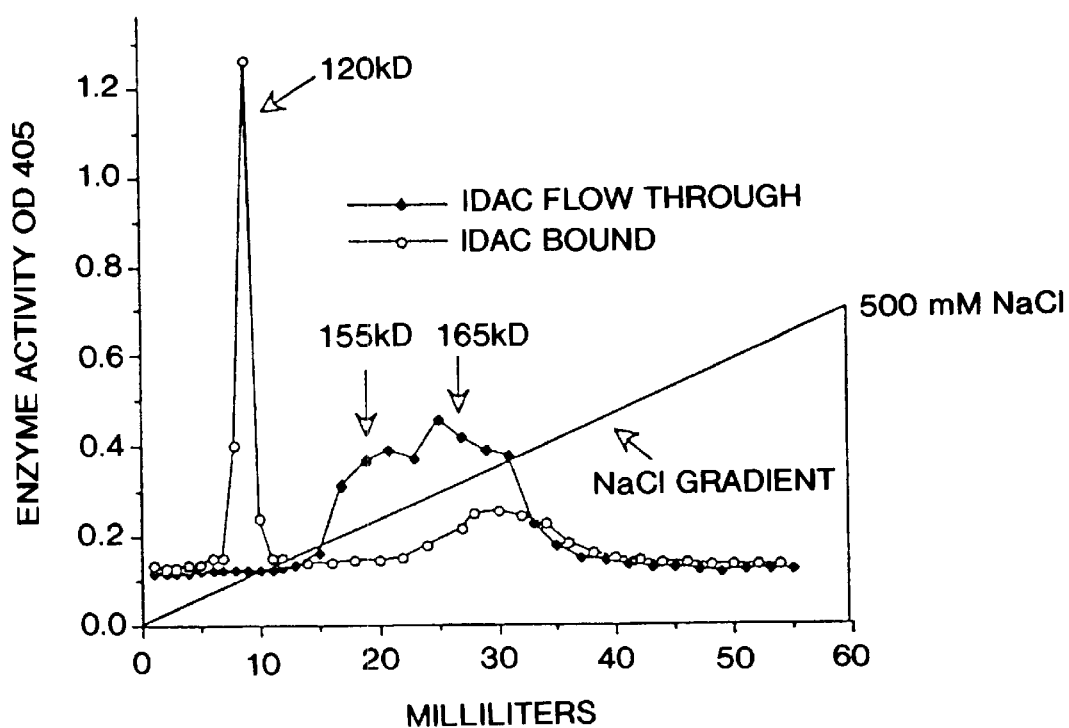
FIG. 16 is a graph of GTVap activity following an anion exchange enzyme activity profile of WGA- and IDAC-purified GTVap: IDAC flow through (solid diamonds); IDAC bound (open circles)

The IDAC flow-through and the IDAC bound fractions were separately chromatographed on a 1 ml Resource Q anion exchange resin as described above. The results, shown in FIG. 16, demonstrate that the zinc-loaded IDAC column binds all of the GTVap-120, whereas most of the GTVap-155 and GTVap-165 flow through. This observation is confirmed by Western blot analysis of these fractions (data not shown). Since binding to zinc likely involves the coordination of protein histidyl residues with the bound zinc ions, it may be that the more heavily glycosylated GTVap's may be sterically hindered from binding to immobilized zinc. The fraction of the GTVap-155 and GTVap-165 that does bind to the zinc columns might be dimerized with GTVap-120 and may not interact directly with the zinc. Previous biophysical studies on other aminopeptidase suggest that these enzymes may exist as dimers.

In summary, the GTVap-120, GTVap-155, and GTVap-165 are enzymatically active, all react with the GTVap1 antibody and can be enriched and separated by the purification scheme described above.

GTVap translocates to the plasma membrane in response to insulin

GLUT4 is known to translocate from an intracellular vesicular compartment to the plasma membrane upon insulin stimulation. In order to determine if GTVap also translocates, adipocytes dissociated from rat epididymal fat pads prepared as described above were stimulated with insulin. Insulin (10 nM) was added to freshly prepared adipocytes which were maintained for 20 minutes at 37° C.

Figure 17:
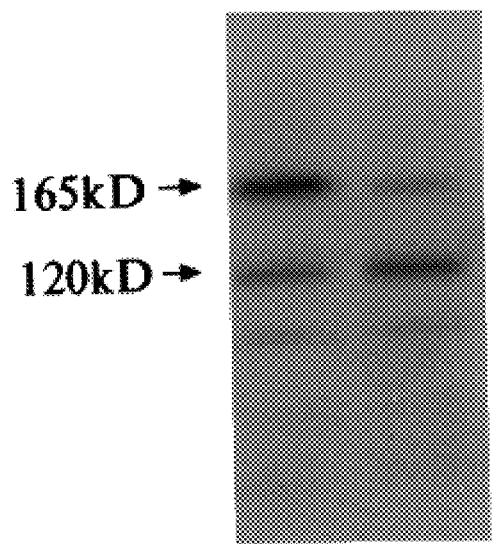
FIG. 17 is a Western blot of GTVap from the plasma membrane fraction following insulin stimulation.
Figure 18:
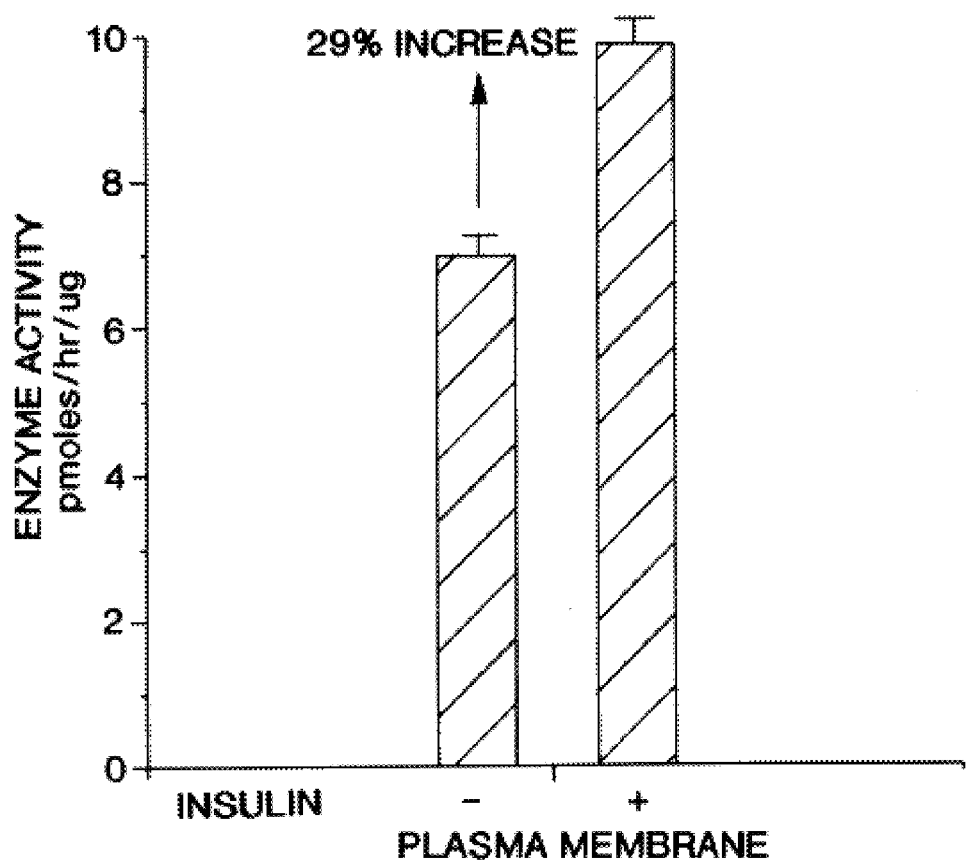
FIG. 18 is a graph of GTVap activity in the plasma membrane following insulin stimulation.

The adipocytes were then washed in TES buffer. The insulin stimulated and control adipocytes were fractionated into the subcellular compartments and analyzed for GTVap enzyme and protein (Western blot) as previously described. FIG. 17 indicates that GTVap translocates to the plasma membrane in response to insulin stimulation as evidenced by increased Western blot reactivity. FIG. 18 indicates that GTVap enzyme activity increases 29% in the plasma membrane following insulin stimulation.

GTVap cleavage of insulin and synthetic peptide substrates

HDM (1.8 mg/ml) was incubated at 37° C. with 120 μg/ml porcine insulin in 50 mM sodium borate, pH 7.5, containing the following protease inhibitors that were previously shown to have no inhibitory effect on GTVap: 2 mM benzamidine, 2 μM leupeptin, 1 μM pepstatin, 1 mM DFP, and 150 μM PMSF. The reaction was terminated after various incubation times by centrifugation of aliquots at 200,000×g to remove the HDM. The insulin products were detected by mass spectrometry or were first chromatographed on a 2.1×5 cm Beckman Spherisorb C18 column at 0.25 ml/min. in a 4 hour linear gradient of 27% to 31% acetonitrile in 1% TFA adjusted to pH 3.0 with TEA, prior to mass spectroscopic analysis.

Figure 19A:
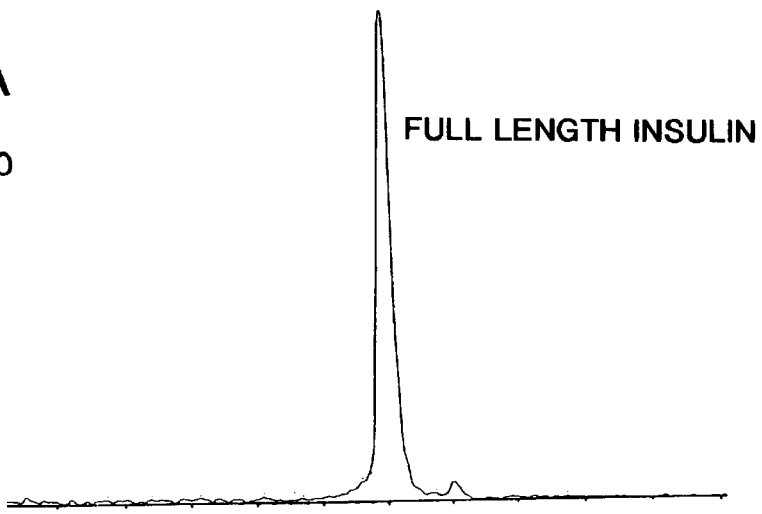
FIGS. 19A–C are graphs of the mass analysis of insulin following digestion with GTVap.
Figure 19B:
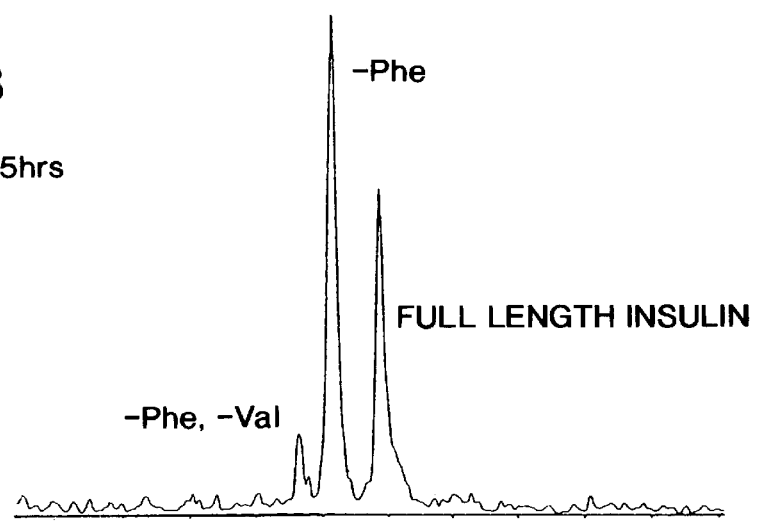
Figure 19C:
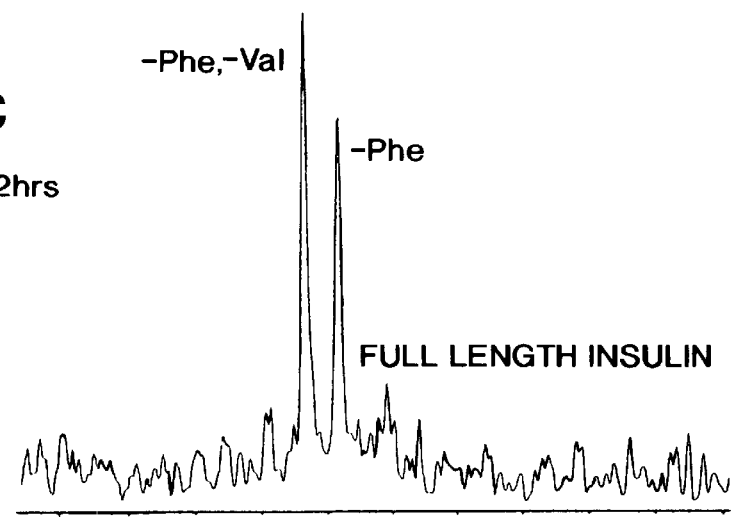
Figure 20:
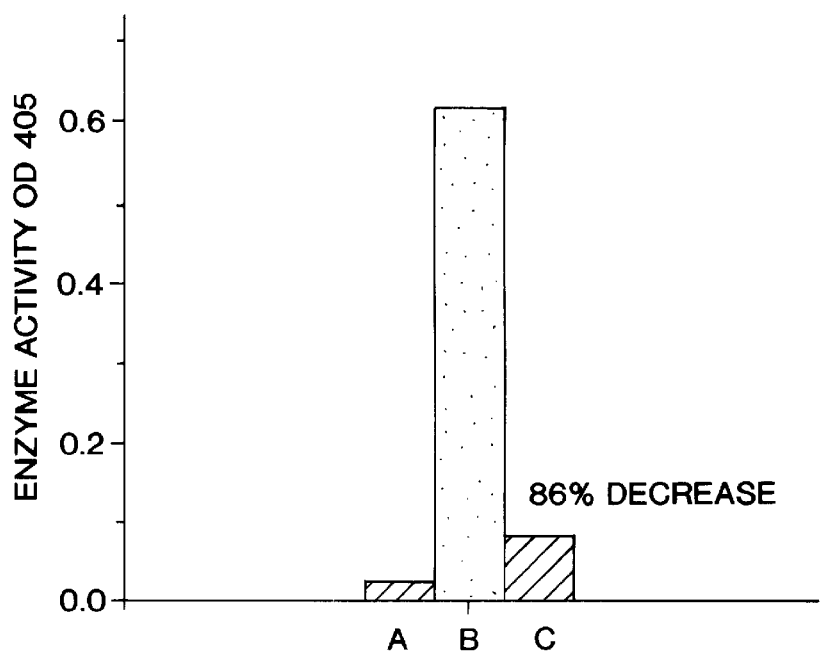
FIG. 20 is a graph showing the inhibition of enzyme activity by GLUT4 vesicle extract: A represents GLUT 4 vesicle extract (25 $\mu$l); B represents WGA bound enzyme activity (25 $\mu$l); C represents WGA bound activity plus extract (25 $\mu$l each)

Using this method both intact and Triton X-100 extracted HDM were shown to have aminopeptidase activity towards insulin. As shown in FIGS. 19a, b, and c, mass spectroscopic analysis indicated that the N-terminal residues phenylalanine and valine of the B-subunit of insulin were removed sequentially from the intact insulin molecule.

The identification of a natural inhibitor of GTVap activity

During the course of this work it was noted that WGA purification of GTVap from Triton X-100 extracted GLUT4 vesicles results in a 10 fold increase in the purified GTVap activity compared to the starting unpurified material.

Figure 21:
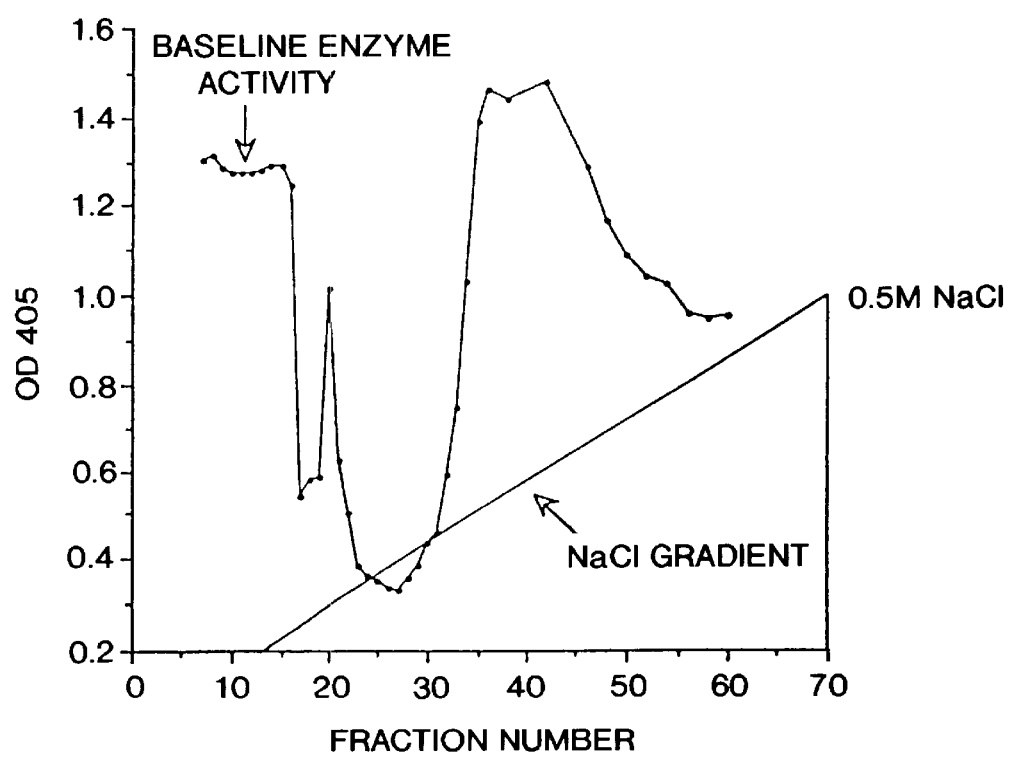
FIG. 21 is a graph showing the ion exchange chromatographic properties of a naturally-occurring GTVap inhibitor.

In order to directly test for inhibitors in the unpurified vesicle extract, fresh GLUT4 vesicle extract was added to WGA purified GTVap. The results indicate that the unpurified extract inhibits the partially purified GTVap enzyme by 86%, as shown in FIG. 21. GLUT4 vesicles thus appear to contain a natural inhibitor of GTVap. This natural inhibitor may be responsible for the relatively low level of GTVap enzyme activity in LDM (the source of GLUT4 vesicles) when compared with the GTVap activity of the HDM or PM.

In order to further purify the inhibitor, the unbound WGA fraction (which contains the inhibitor) from LDM was chromatographed on a Resource Q column at 4° C. in 20 mM Tris-HCl, 0.1% Triton X-100, pH 7.5. Aliquots (25 μl) of WGA purified GTVap (which serves as the uninhibited enzyme) were added to microtiter plate wells, followed by 75 μl from each fraction from the ion exchange separation. To each well was added 100 μl of 20 mM Tris-HCl, 0.1% Triton X-100, pH 7.5 and all wells were incubated for 30 minutes. Leucine-p-nitroanilide was then added to a final concentration of 1.6 mM and GTvap activity was measured. As shown in FIG. 21, fractions 15–35 show GTVap inhibitory activity.

Gel filtration analysis indicates that the inhibitor has a molecular weight of between 10 kD and 20 kD (data not shown).

Other embodiments of the invention will be apparent to the skilled in the art from a consideration of this specification or practice of the invention disclosed herein. It is intended that the specification and examples be considered as exemplary only, with the true scope and spirit of the invention being indicated by the following claims.

---

We claim:

1. A method for identifying modulators of GTVap activity, comprising the following steps:
   (a) providing GTVap or GTVap-containing material having an assayable amount of enzymatic activity;
   (b) incubating said GTVap or GTVap-containing material with a test substance to be assayed for ability to modulate GTVap activity;
   (c) adding a GTVap substrate;
   (d) monitoring GTVap activity as a function of time; and
   (e) determining the modulatory effect of said test substance on GTVap.

2. The method of claim 1, wherein said GTvap or GTvap-containing material having an assayable amount of enzymatic activity is obtained from adipose tissue, skeletal muscle tissue, cardiac muscle, cell lines derived from these tissues, or from a recombinant source.

3. The method of claim 1, wherein in said step of adding a GTVap substrate, leucine-p-nitroanilide or a polypeptide substrate is employed.

4. The method of claim 3, wherein said polypeptide is insulin.

* * * * *